US008663192B2

(12) United States Patent
Hester et al.

(10) Patent No.: US 8,663,192 B2
(45) Date of Patent: Mar. 4, 2014

(54) DEVICES AND METHODS FOR TREATING PAIN ASSOCIATED WITH TONSILLECTOMIES

(75) Inventors: Jerome E. Hester, Menlo Park, CA (US); Anthony J. Abbate, Santa Clara, CA (US); Richard E. Kaufman, Los Gatos, CA (US); David C. Gale, San Jose, CA (US); Gail M. Zaler, Milpitas, CA (US); Bin Huang, Pleasanton, CA (US); Lisa Earnhardt, Menlo Park, CA (US); Vijaykumar Rajasekhar, Apple Valley, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 8 days.

(21) Appl. No.: 12/768,628

(22) Filed: Apr. 27, 2010

(65) Prior Publication Data
US 2011/0112513 A1    May 12, 2011

Related U.S. Application Data

(60) Provisional application No. 61/173,093, filed on Apr. 27, 2009.

(51) Int. Cl.
*A61M 31/00* (2006.01)
(52) U.S. Cl.
USPC .......................................... 604/514
(58) Field of Classification Search
USPC ........................................ 604/514; 606/110
See application file for complete search history.

(56) References Cited

U.S. PATENT DOCUMENTS

| 7,074,426 | B2 * | 7/2006 | Kochinke ...................... 424/435 |
| 8,025,635 | B2 * | 9/2011 | Eaton et al. ................ 604/94.01 |
| 2007/0005094 | A1 * | 1/2007 | Eaton et al. ................... 606/199 |
| 2007/0293946 | A1 * | 12/2007 | Gonzales et al. ............... 623/10 |
| 2008/0195037 | A1 | 8/2008 | Hissong et al. |
| 2008/0215090 | A1 | 9/2008 | Gonzales et al. |

(Continued)

FOREIGN PATENT DOCUMENTS

CN  1217639 A    5/1999
MD      3445 F1   12/2007

(Continued)

OTHER PUBLICATIONS

Seltzer, A.P. (Jul. 1969). "Control of Tonsillar Hemorrhage. Use of a New Cellulose Material," *Journal of the National Medical Association* 61(4):333-334.

(Continued)

*Primary Examiner* — Nicholas Lucchesi
*Assistant Examiner* — Diva K Chander
(74) *Attorney, Agent, or Firm* — Morrison & Foerster LLP

(57) ABSTRACT

Described here are devices and methods for treating one or more conditions or symptoms associated with a tonsil procedure. In some variations, a drug-releasing device may be at least partially delivered to one or more tonsillar tissues before, during, or after a tonsil procedure. In some variations, the drug-releasing device may be configured to be biodegradable. In other variations, the drug-releasing device may comprise one or more hemostatic materials or one or more adhesives. The drug-releasing device may be configured to release one or more drugs or agents, such as, for example, one or more analgesics, local anesthetics, vasoconstrictors, antibiotics, combinations thereof and the like.

29 Claims, 12 Drawing Sheets

(56) References Cited

U.S. PATENT DOCUMENTS

| | | |
|---|---|---|
| 2009/0084389 A1 | 4/2009 | Gonzales |
| 2009/0181074 A1 | 7/2009 | Makower et al. |
| 2009/0210005 A1 | 8/2009 | Dinger, III et al. |
| 2011/0020768 A1 | 1/2011 | Spagnoli et al. |
| 2011/0166598 A1 | 7/2011 | Gonazles et al. |

FOREIGN PATENT DOCUMENTS

| | | |
|---|---|---|
| WO | WO-97/41786 A2 | 11/1997 |
| WO | WO-97/41786 A3 | 11/1997 |
| WO | WO-2009/029692 A1 | 3/2009 |
| WO | WO-2010/126912 A1 | 11/2010 |

OTHER PUBLICATIONS

International Search Report mailed on Jun. 28, 2010, for PCT Patent Application No. PCT/US2010/032630, filed on Apr. 27, 2010, 2 pages.

Written Opinion mailed on Jun. 28, 2010, for PCT Patent Application No. PCT/US2010/032630, filed on Apr. 27, 2010, 5 pages.

\* cited by examiner

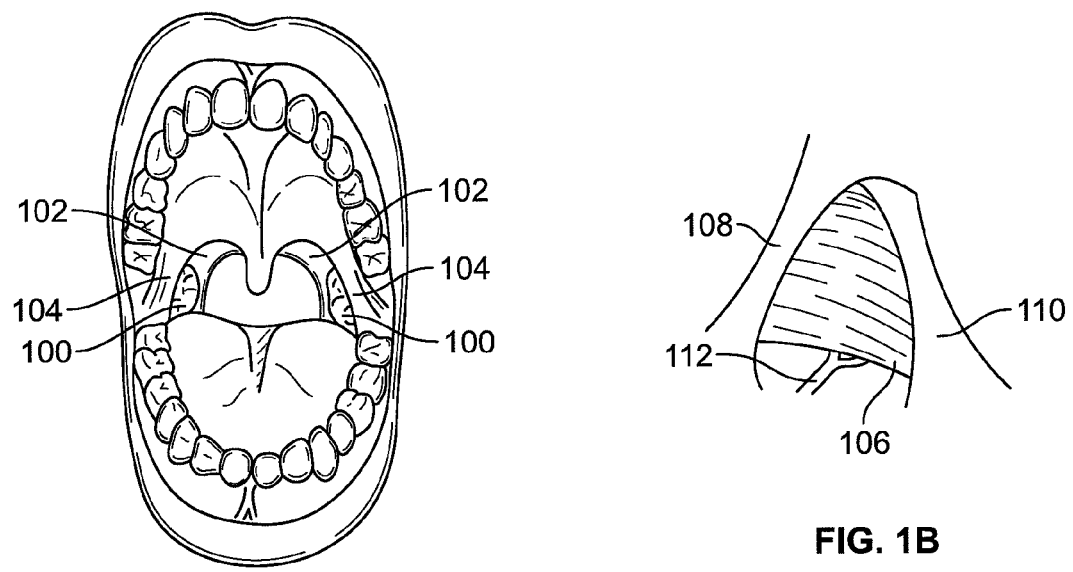
FIG. 1A
FIG. 1B
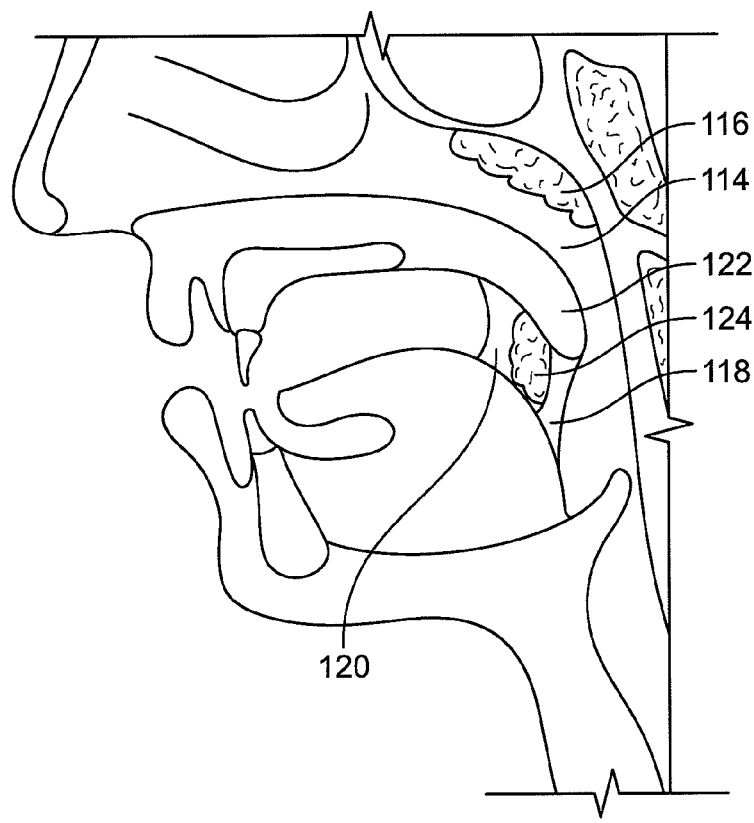
FIG. 1C

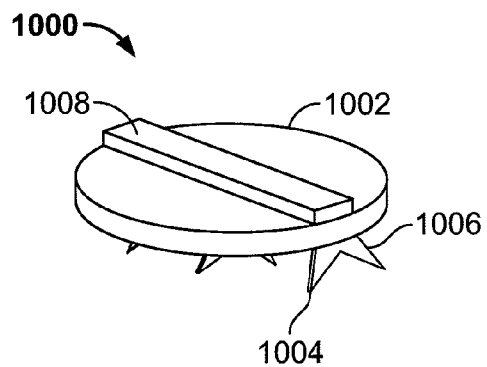
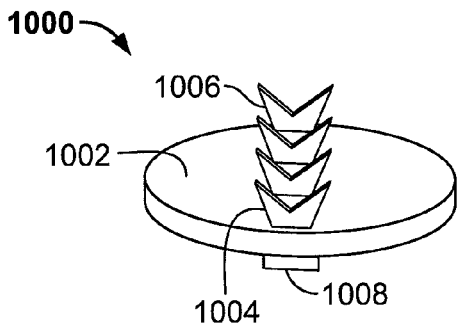
FIG. 10A  FIG. 10B
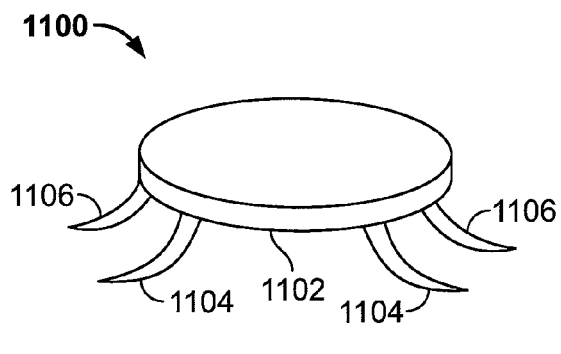
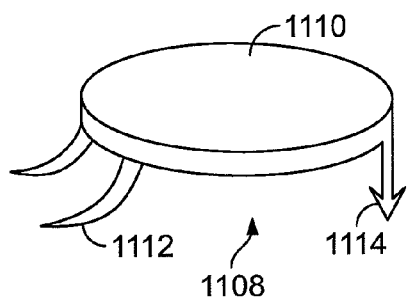
FIG. 11A  FIG. 11B
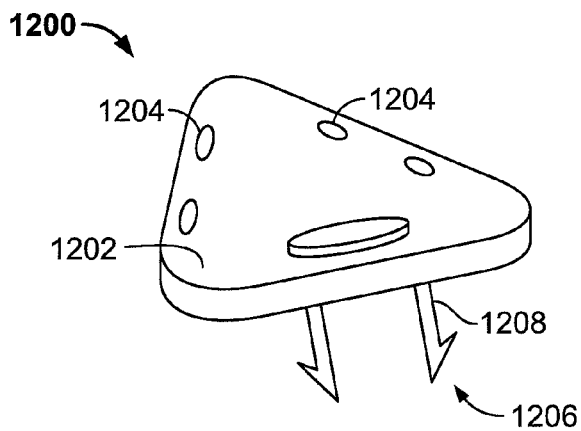
FIG. 12

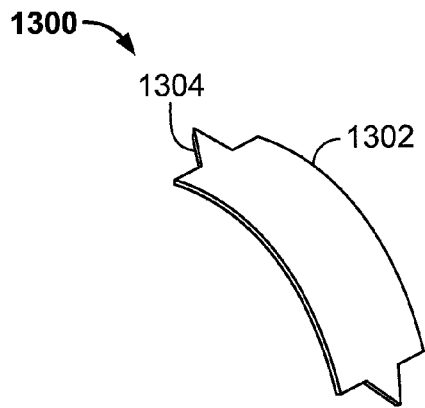
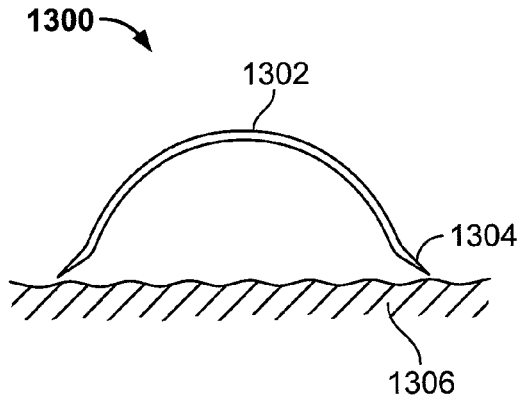
FIG. 13A    FIG. 13B
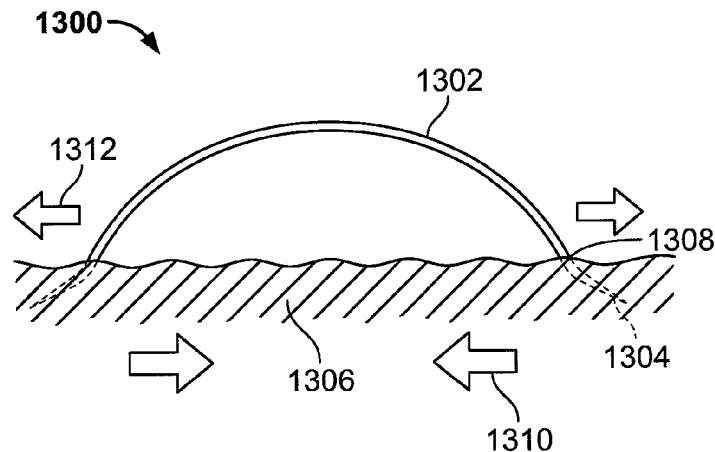
FIG. 13C
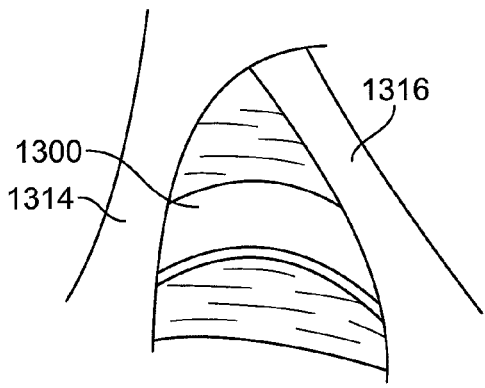
FIG. 13D

DEVICES AND METHODS FOR TREATING PAIN ASSOCIATED WITH TONSILLECTOMIES

CROSS-REFERENCE TO RELATED APPLICATIONS

This application claims priority to U.S. Provisional Patent Application Ser. No. 61/173,093, filed on Apr. 27, 2009 and titled "DEVICES AND METHODS FOR TREATING PAIN ASSOCIATED WITH TONSILLECTOMIES," which is incorporated by reference herein in its entirety.

FIELD

The present invention relates generally to devices and methods for the treatment of one or more tonsils, adenoids, and/or surrounding tissue.

BACKGROUND

One of the oldest known surgical procedures, a tonsillectomy is an operation during which one or more portions of the palatine tonsils ("tonsils") are removed. An adenoidectomy is a procedure during which one or more portions of the pharyngeal tonsils ("adenoids") are removed. Tonsillectomies and adenoidectomies are usually performed to alleviate one or more symptoms that may be associated with infected or enlarged tonsils or adenoids, such as chronic sore throats, recurring strep throat, abscesses, upper airway obstructions, ear infections, bad breath, and sleep apnea. Tissue may be removed in one of many ways, such as cold dissection, electrocautery removal, laser removal, coblation, microdebriding, radiofrequency ablation, and harmonic scalpel dissection.

Tonsillectomies and adenoidectomies are very common, with over 800,000 procedures being performed each year in the United States. Despite the frequency of these procedures, as well as the varied means by which they are performed, tonsillectomies and adenoidectomies are still associated with a great deal of post-operative pain and discomfort. More specifically, there is usually a seven- to ten-day recovery period during which a patient may experience pain, discomfort, dehydration and weight loss. Additionally, there is an approximately 1-7% rate of post-operative hemorrhaging, as well as a risk of infection.

Little has been done to successfully reduce the pain or discomfort following a tonsillectomy or adenoidectomy. Generally, a physician will prescribe antibiotics and narcotics (e.g., acetaminophen, codeine) for post-operative pain. Oral administration of such antibiotics and narcotics may be undesirable, as swallowing may be extremely painful for a patient. Additionally, the amount of narcotic ingested may yield other undesirable side effects, such as drowsiness, dizziness, lightheadedness, or other complications that result from the exposure of the entire body to the effects of the narcotic. Other post-operative treatment methods, including topical, intravenous, intralesional and oral administration of narcotics, non-steroidal ant-inflammatory drugs (NSAIDS), steroids, and/or local anesthetics have been minimally effective at reducing pain or discomfort. As such, it would be desirable to provide a more effective way of reducing pain or discomfort following a tonsil procedure (e.g., a tonsillectomy, adenoidectomy, or the like).

BRIEF SUMMARY

Described here are devices and methods for treating the tonsils, adenoids, and/or surrounding tissue. Generally, one or more devices are attached to or implanted in or around tissue, and may be configured to release one or more drugs to the tonsil or adenoids. In some variations, the devices are used to treat an inflamed or enlarged tonsil or adenoids. In other variations, the devices are used to aid in post-operative recovery following a tonsillectomy or adenoidectomy (e.g., by locally delivering one or more drugs, by covering or manipulating exposed tissue, etc.).

In some variations, one or more sutures or suture-like materials may be at least partially implanted in tonsillar tissue. In some of these variations, the one or more sutures are configured to release one or more drugs to the tonsils. In other variations, the suture is configured to self-anchor within tissue (e.g., the suture may comprise one or more unidirectional elements that allow suture to be pulled through tissue in a first direction, but resist movement in an opposite direction). In still other variations, the suture is biodegradable.

In other variations, one or more tissue-piercing devices may implanted into, around, or adjacent to tonsillar tissue. Generally the tissue-piercing devices are designed to pierce, puncture, or otherwise penetrate tissue. In some of these variations, the tissue-piercing devices comprise one or more filaments, spikes, or staples. In some variations, the tissue-piercing devices are configured to resist removal from tissue. In some of these variations, the tissue-piercing devices comprise one or more barbs, prongs, notches, threading, or a combination thereof.

In still other variations, one or more clips may be attached to tonsillar tissue. Generally the clips may comprise a surface member and one or more anchoring members. In some of these variations, the surface member and anchoring members may be formed from a single piece of material. In other variations, one or more sutures or tissue-piercing devices may be used to attach the surface member to tissue.

In other variations, one or more tissue-restraining devices may be applied to tonsillar tissue. In some of these variations, the tissue-restraining device may be configured to stretch an area of tissue. In other variations, the tissue-restraining device may be configured to help prevent movement of one or more tissues. The tissue-restraining device may comprise a body member, and may additionally comprise one or more anchors. Anchors may be used to attach the tissue-restraining device to tissue, and may have any suitable configuration of elements, as described in more detail below.

In some variations, a plurality of space-filling implants may be used to fill one or more spaces within tonsillar tissue. The space-filling implants may comprise one or more beads, pellets, seeds, capsules, or a combination thereof. The space-filling implants may self-assemble to conform to the shape of one or more spaces within tonsillar tissue. In some variations, one or more space-filling implants may be configured to burst upon application of one or more forces or stimuli thereto.

BRIEF DESCRIPTION OF THE DRAWINGS

FIGS. 1A-1C are illustrations of the tonsils, adenoids, and their surrounding anatomy.

FIGS. 10A, 10B, 11A, 11B and 12 are illustrative depictions of variations of devices comprising a clip.

FIGS. 13A-13D, 14, 15, 16A, 16B, 17, 18A and 18B are illustrative depictions of variations of devices that are configured to stretch or restrain tissue.

DETAILED DESCRIPTION

Figure 2A:
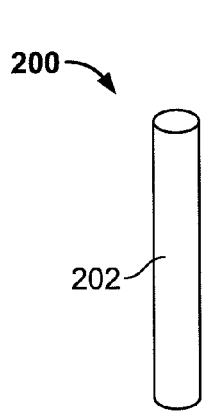
FIGS. 2A-2K depict illustrative variations of tissue-piercing devices.

The palatine tonsils ("tonsils") and pharyngeal tonsils ("adenoids") are masses of lymphoid tissues that help protect the body against infection. FIGS. 1A-1C illustrate the tonsils and adenoids, as well as their surrounding anatomy. The tonsils are located in the throat, and can be seen through the mouth, as illustrated in FIG. 1A. Shown there are palatine tonsils (100), the palatopharyngeal arch (102), and the palatoglossal arch (104). The palatopharyngeal arch (102) comprises mucosa overlaying the palatopharyngeus muscle, while the palatoglossal arch (104) comprises mucosa overlaying the palatoglossus muscle. The palatoglossus and palatopharyngeus muscles, together with the superior constrictor muscle, make up the tonsillar fossa. FIG. 1B shows a perspective view of the tonsillar fossa. Shown there is superior constrictor muscle (106), palatoglossus muscle (108), and palatopharyngeus muscle (110). Also shown there is glossopharyngeal nerve (112), which sits in the outer wall of the pharynx (not shown) beneath the superior constrictor muscle (106). Generally, the glossopharyngeal nerve (112) is a cranial nerve that innervates the tonsils and a portion of the tongue.

The tonsillar fossa forms a "tonsillar bed" for the tonsils, and the tonsils are connected thereto. Specifically, the tonsils lay on the superior constrictor muscle (106), and are bounded posteriorly by the palatopharyngeus muscle (110) and anteriorly by the palatoglossus muscle (108). During a tonsillectomy, a surgeon separates at least a portion of the tonsils from the muscles of the tonsillar fossa while attempting to minimize damage done to the tonsillar fossa. If the tonsillar bed is punctured during a tonsillectomy, the glossopharyngeal nerve may be injured. Once the tonsils are removed, one or more portions of the mucosa of the palatopharyngeal or palatoglossal arch ("mucosal flaps") may be pulled over the exposed tissue and sutured into place, thereby sealing off the operation site.

The adenoids, on the other hand, are located behind the nasal passages in the nasopharynx. FIG. 1C shows a sagittal cross-section of a portion of the head and throat. Shown there is nasopharynx (114) housing adenoid (116). Also shown there are the palatopharyngeal (118) and palatoglossal (120) arches descending from soft palate (122) and surrounding tonsil (124). Adenoidectomies are similar to tonsillectomies in that the adenoids are separated from surrounding tissue and removed through the mouth.

Generally described here are devices and methods for treating one or more areas of tonsillar tissue. When reference is made to the term "tonsillar tissue" herein, it should be understood that such tonsillar tissue can include, without limitation, any portions of the palatine tonsils, adenoids, lingual tonsils, tubal tonsils, tonsillar fossa (e.g., palatopharyngeal arch, palatoglossal arch, superior constrictor muscle), or other surrounding tissue (e.g., muscles, fascia, connective tissue). In some instances, the devices described here may be used to treat one or more inflamed or infected tonsils. In other instances, the devices and methods may aid in recovery following a tonsil procedure. When reference is made to the term "tonsil procedure" herein, it should be understood that such tonsil procedures can include, without limitation, any procedure such as tonsillectomies, adenoidectomies, lingual tonsillectomies, other treatments for sleep apnea, tonsillitis, or other tonsil conditions, and the like. The devices and methods may help to minimize post-operative pain or discomfort, may help prevent post-operative infection or hemorrhaging, may shorten healing or recovery time, may do combinations thereof, or the like.

Devices

Described here are devices for treating one or more portions of tonsillar tissue. In some variations, the devices may be used to treat tonsillar tissue during or following a tonsil procedure. The devices may be configured to release one or more drugs or agents to tonsillar tissue, but need not. The terms "drugs" or "agents" are used interchangeably throughout, and it should be understood that such drugs or agents may include, without limitation, any suitable chemical substance or compound, whether active or inert. Additionally, the devices may or may not be configured to biodegrade, bioerode, or otherwise break down. In some variations, one or more portions of the device may be configured to be implanted into tissue. In some of these variations, one or more portions of the device may be configured to puncture, pierce, or otherwise penetrate tissue. In other variations, one or more portions of the device may be configured to shield or cover one or more areas of tonsillar tissue. In still other variations, the devices may be configured to immobilize, stretch, compress, tension, approximate or otherwise manipulate tissue or tissues.

The devices may have any suitable size, shape, or configuration of elements. In some variations, one or more portions of the device may be solid. In other variations, one or more portions of the device may be semi-solid. The devices, or one or more elements thereof, may include, but are not limited to, one or more sutures, strands, threads, ribbons, filaments, fibers, rods, tubes, spikes, staples, clips, gels, foams, emulsions, beads, pellets, meshes, patches, sheets, films, combinations thereof, and the like. These various devices and components will be described in more detail below.

Any of the devices described here may be delivered to tonsillar tissue in any suitable way. In some variations, at least a portion of the device is implanted into tissue. In some of these variations, the entire device may be implanted into tonsillar tissue. In other variations, one or more portions of the device may be implanted into tonsillar tissue. In some of these variations, different portions of the device may be implanted in different areas of tonsillar tissue. For example, in some variations one or more portions of a device may be implanted in tissue of the palatoglossal arch while another portion of the device may be implanted in tissue of the palatopharyngeal arch. When a portion of a device is implanted into tissue, that portion may be placed inside of an opening or space inside of a tissue, beneath a tissue, between tissues, or combinations thereof. When a device is placed in an opening or space inside of tissue, this opening or space may be naturally occurring or artificially formed. In other variations, at least a portion of the device may be placed on, against, near or adjacent tissue. In these variations, the portion of the device may be held in place in any suitable manner. In some variations, one or more portions of the device or separate components may be used to anchor the device to tissue. In other variations, one or more portions of the device adhere to tissue. In still other variations, the surrounding tissue may be manipulated to surround or otherwise engage the one or more portions of the device. For example, if a mucosal flap is pulled and sealed to cover exposed tonsillar tissue during a tonsillectomy, the mucosal flap may be used to cover at least a portion of a device. In other instances, the palatoglossal and palatopharyngeal arches may be brought and held closer together, which may help to hold a portion of a device between the arches.

Sutures

In some variations, one or more sutures or suture-like materials (e.g., yarns, threads, cords, ribbons and the like, collectively referred to as "sutures" herein) may be delivered to tonsillar tissue. The sutures may or may not be configured to deliver one or more drugs to the tonsillar tissue. When the suture is configured to deliver one or more drugs, the suture may deliver drug in any suitable manner, as will be described in more detail below. Additionally, the suture may or may not be configured to biodegrade, bioerode, or otherwise break down. The suture may additionally include one or more features to aid in placement or retention in tissue. For example, in some variations the suture may be configured to self-anchor inside of tissue. More specifically, the suture may comprise one or more unidirectional anchors, flaps, barbs, or other elements that allow the suture to be pulled through tissue in one direction, but resist movement in an opposite direction. In this way, a suture may be threaded at least partially through one or more areas of tonsillar tissue, but may resist being pulled out of the tissue.

One or more sutures may be applied to tonsillar tissues in any suitable manner. In some instances, one or more sutures may be used to anchor or otherwise attach at least a portion of one or more devices to tissue. In other instances, one or more sutures may be used to join or attach two or more areas of tissue. For example, in instances where the mucosal flaps are pulled over exposed tonsillar tissue, one or more of the sutures described above may be used to suture the mucosal flaps in place. In other instances, one or more sutures may be used to approximate or otherwise reduce the distance between the palatoglossal and palatopharyngeal arches. This may help open the airway into the throat, and may further assist in treating breathing disorders such as obstructive sleep apnea. In still other instances, one or more sutures may be stitched, advanced, or otherwise placed throughout one or more regions of tonsillar tissue. In variations where the one or more sutures are configured to release one or more drugs, placement in or throughout one or more tissues allows the suture to provide drugs to those regions of tonsillar tissue. To place a suture in a region of tissue, the suture may be attached to a needle or other structure, and the needle or other structure may be pulled through a volume of tissue to introduce the suture thereto. In other instances, the distal end of a cannula or tube (e.g., a hypotube) may be advanced into a volume of tissue, and a length of suture can be ejected from the cannula or tube into the tissue.

Tissue-Piercing Devices

In some variations of the devices described here, the device may be configured to pierce, puncture, or otherwise penetrate tonsillar tissue. It should be noted, however, that although these tissue-piercing devices may be configured to penetrate tissue, they need not be used in practice to penetrate tissue. In some instances, one or more tissue-piercing devices may be held against an area of tissue by one or more patches, meshes, films or sheets, such as those described below. When used to penetrate tissue, the tissue-piercing device may penetrate tissue in order to facilitate implantation in tonsillar tissue.

Each tissue-piercing device may have any suitable size, shape, and configuration of elements. The tissue-piercing devices may or may not be configured to release one or more drugs. When configured to release one or more drugs, the tissue-piercing device may release any suitable drug or drugs in any suitable manner, as will be described in more detail below. Additionally, the tissue-piercing device may or may not be configured to biodegrade, bioerode, or otherwise break down, and may be made from any suitable material or combination of materials, such as those described below. The tissue-piercing device may be substantially rigid, but need not be. Indeed, one or more portions of the tissue-piercing device may be flexible. In some variations, the tissue-piercing device may comprise one or more flexible portions and one or more rigid portions.

Figure 2B:
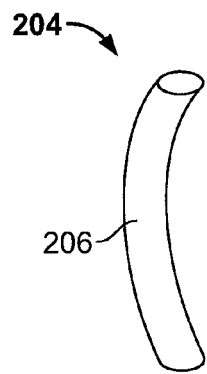

FIGS. 2A-2K illustrate several suitable variations of tissue-piercing devices. FIG. 2A illustrates one such variation of tissue-piercing device (200) comprising filament (202). While shown in FIG. 2A as being a filament (202), any suitable bar, fiber, tube, or rod-like structure may be used. Tissue-piercing device (200) may be inserted into tissue by pushing one end of tissue-piercing device (200) against tissue. While shown in FIG. 2A as having a circular cross-section, filament (202) may have any suitable cross-sectional shape, such as, for example, an oval, a triangle, a rectangle, a polygon, or a shape with irregular geometry. Additionally, while shown in FIG. 2A as being straight, filament (202) need not. Indeed, a filament (202) may have one or more curves, bends, twists, or kinks. For example, FIG. 2B illustrates a variation of tissue-piercing device (204) comprising a curved filament (206). In these variations, the curved filament (206) may have any suitable radius of curvature. Additionally, such a curved configuration may reduce the depth to which tissue-piercing device (204) may pierce. For example, when a tissue-piercing device (204) is placed in the tonsillar bed, it may be desirable to limit the penetration depth to reduce the likelihood that a tissue-piercing device (204) puncture or otherwise damage one or more nerves (e.g. the glossopharyngeal nerve) or blood vessels (e.g. the carotid artery).

Figure 2C:
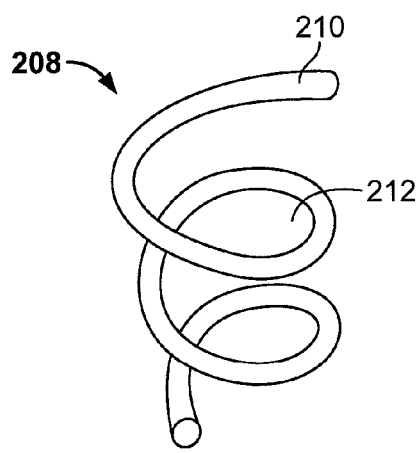

FIG. 2C illustrates another variation of a tissue-piercing device (208) comprising a filament (210) that is wound into a coil having loops (212). In these variations, the coiled filament (210) may comprise any number of loops (212), and each loop (212) may have any suitable diameter. The coiled filament (210) may take on any suitable overall shape. In some variations, the coiled filament (210) may be wound into a generally cylindrical shape, such as tissue-piercing device (208) shown in FIG. 2C. In other variations, the coiled filament (210) may be wound into a generally conical or frusto-conical shape, or may be wound into an hourglass shape.

Figure 2D:
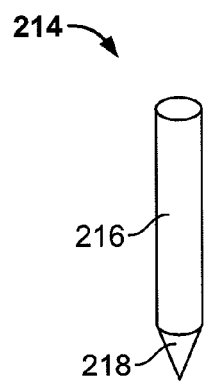
Figure 2E:
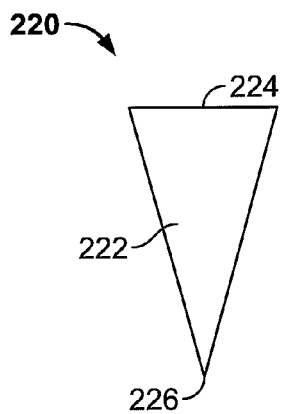
Figure 2F:
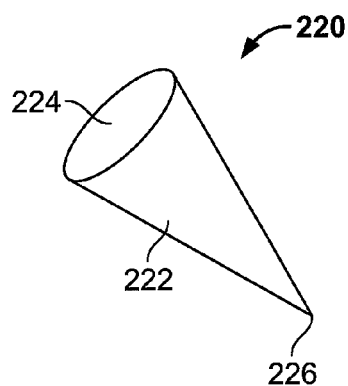

While the tissue-piercing devices shown in FIGS. 2A-2C have constant cross-sectional areas, they need not. Indeed, the cross-sectional area of a tissue-piercing device may vary through one or more portions of the device. FIG. 2D shows one such variation of tissue-piercing device (214) comprising a filament (216) with a tapered end (218). Tapered end (218) may aid the tissue-piercing device (214) in piercing, puncturing, or otherwise penetrating tissue. In other variations, the cross-sectional area of the tissue-piercing device may vary along its entire length. FIGS. 2E and 2F show a side view and a perspective view, respectively, of one such variation of tissue-piercing device (220). Shown there is spike (222), in which the cross-sectional area decreases from a proximal end (224) to its distal end (226). The reduced cross-sectional area of the distal end (226) may aid tissue-piercing device (220) in piercing, puncturing, or otherwise penetrating tissue.

Figure 2G:
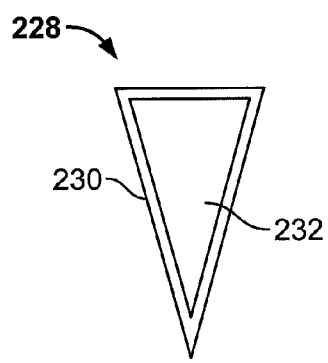

A tissue-piercing device may be solid, or may be at least partially hollow. Indeed, a tissue-piercing device may comprise one or more pores, cavities, channels, or other spaces within the device's body. FIG. 2G shows a cross-sectional side view of one such variation of tissue-piercing device (228) comprising a spike (230) with cavity (232) therein. Tissue-piercing device (228) may comprise any number of cavities (232), and each cavity (232) may have any suitable size, shape, and positioning within the tissue-piercing device (228). In variations where tissue-piercing devices (228) comprise one or more cavities (232), one or more of the cavities (232) may act as a reservoir for one or more solutions, powders, solids, foams, gels, or a combination thereof, which may or may not comprise one or more drugs.

Figure 2H:
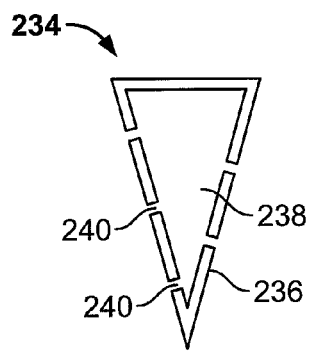

In variations where the cavity (232) holds one or more drugs or drug-containing materials, one or more drugs may diffuse or otherwise migrate from cavity (232) through the body of the tissue-piercing device (228). In variations where the tissue-piercing device (228) is configured to biodegrade, bioerode, or break down, degradation of the device (228) may expose one or more portions of the cavity (232). Once exposed, one or more drugs or materials may be released from the cavity (232). FIG. 2H illustrates another variation of tissue-piercing device (234) comprising spike (236) with cavity (238) and channels (240) therein. In these variations, one or more channels (240) may pass from cavity (238) through the body of spike (236). In some instances, one or more drugs or materials held in cavity (238) may exit tissue-piercing device (234) through one or more of the channels (240). Tissue-piercing device (234) may comprise any number of channels (240), and each channel (240) may have any suitable size or cross-sectional shape. The number of channels (240), the size and shape of each channel (240), and the nature of the drug or material held within cavity (238) may determine the rate at which the drug or material exits the tissue-piercing device. For example, increasing the cross-sectional area of a channel (240) may increase the rate at which a material can pass therethrough.

Figure 2I:
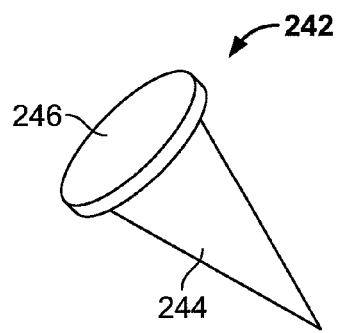
Figure 2J:
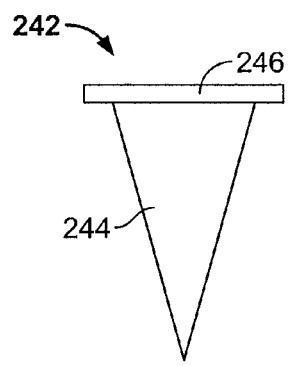

The tissue-piercing device may additionally include one or more elements that are configured to engage one or more surfaces. For example, FIGS. 2I and 2J show a side view and a perspective view, respectively, of tissue-piercing device (242) having spike (244) and base member (246). When spike of (244) of tissue-piercing device (242) is implanted in tonsillar tissue, base member (246) may press against or engage one or more tissue surfaces (not shown). Indeed, the base member (246) may act as a stop, thereby serving to limit the depth that spike (244) is able to penetrate. Limiting the depth of penetration may reduce the likelihood that spike (244) may penetrate deep enough to damage one or more nerves (e.g., the glossopharyngeal nerve) or blood vessels (e.g., the carotid artery) when penetrating the tonsillar bed or surrounding tissue. For example, in some variations the penetration may be less than about 5 mm, less than about 4 mm, less than about 3 mm, less than about 2 mm, or the like. In instances where tissue-piercing device (242) is used to anchor one or more devices to tonsillar tissue, as will be described in more detail below, the base member (242) may engage one or more portions of the one or more devices to hold the one or more devices against tissue.

Figure 2K:
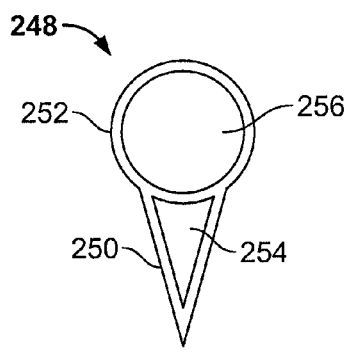

A base member may be any structure suitable to engage a tissue surface, and may have any suitable size or shape. While shown in FIGS. 2I and 2J as being as a circular plate, the base member may be a plate with any suitable shape. In some variations, the base member may comprise a plate with an oval, triangular, rectangular, polygonal, or irregular shape. In other variations, the base member may not be a plate at all. Indeed, in some variations the base member may comprise a sphere, hemisphere, pyramid, box, cube, or a shape with irregular geometry. Additionally, the base member may include one or more cavities or spaces, such as those described above. FIG. 2K illustrates a cross-sectional side view of one such variation of tissue-piercing device (248). Shown there is spike (250) and spherical base member (252), each comprising a cavity ((254) and (256) respectively). Cavities (254) and (256) may be separate, or may be joined via one or more pores or channels (not shown).

Figure 3:
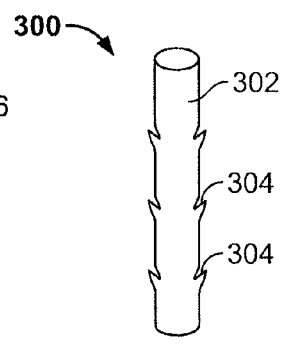
FIG. 3 depicts a variation of a filament comprising notches.

In some variations, the tissue piercing device may include one or more features that may help keep the tissue-piercing device implanted in tissue. In some variations, the overall shape of the tissue-piercing device may help keep the tissue-piercing implanted in tissue, such as the coiled filament (210) shown in FIG. 2C. FIG. 3 illustrates another variation of tissue-piercing device (300). Shown there is filament (302) with notches (304). Notches (304) may allow tissue-piercing device (300) to pass through tissue in one direction, but may resist movement in an opposite direction. Tissue-piercing device (300) may comprise any suitable number of notches (e.g., zero, one, two, three, four, five, or six or more), and each notch may have any suitable size and be at any suitable location on tissue-piercing device (300). The amount that a tissue-piercing device (300) will resist being pulled from tissue may depend, in part, on the number of notches (304), as well as the size of each notch (304). For example, increasing the number of notches (304) may make it more difficult to remove a tissue-piercing device from tissue after it is implanted. Notches (304) may be formed in any suitable manner, such as, for example, cutting or etching the surface of tissue-piercing device (300).

Figure 4A:
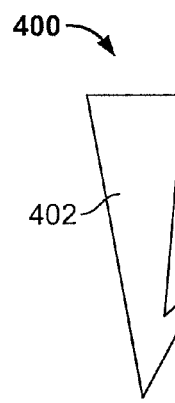
FIGS. 4A-4D show illustrative variations of tissue-piercing devices that are configured to anchor in tissue.
Figure 4B:
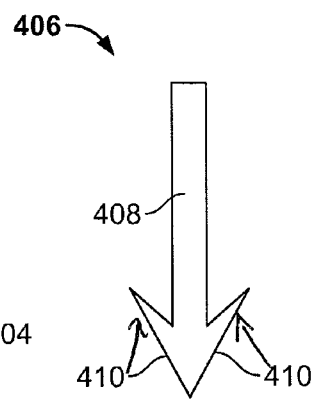
Figure 4C:
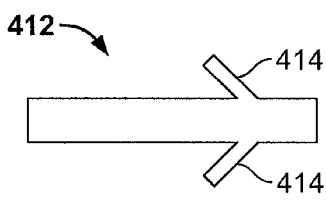
Figure 4D:
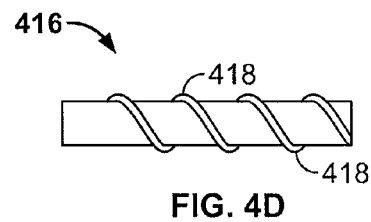

In other variations, a tissue-piercing device comprises one or more barbs, prongs, or other protrusions that allow for unidirectional movement of the tissue-piercing device through tissue. FIG. 4A shows one such variation of tissue-piercing device (400) comprising spike (402) which comprises a barb (404). While shown in FIG. 4A as having only one barb (404), the tissue-piercing device (400) may have any suitable number of barbs (e.g., zero, one, two, three, or four or more). Indeed, FIG. 4B shows one such variation of tissue-piercing device (406) comprising a filament (408) having two barbs (410). FIG. 4C shows another variation of tissue-piercing device (412) comprising angled prongs (414). In still other variations, such as that shown in FIG. 4D, tissue-piercing device (416) comprises threading (418). Threading (418) may allow the tissue-piercing device (416) to be "screwed" into tissue such that the threading (418) engages tissue. This engagement between the threading (418) and tissue may help to prevent the tissue-piercing device (416) from being pulled out of the tissue.

Figure 5:
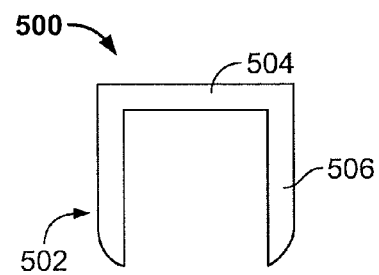
FIG. 5 depicts a variation of a tissue-piercing device comprising a staple.

In some variations, the tissue-piercing device may comprise one or more staples. A staple may be any size or shape, depending on its intended use. FIG. 5 illustrates a suitable variation of tissue-piercing device (500). Shown there is staple (502) comprising base (504) and legs (506). Base (504) and legs (506) may be formed from a single piece of material, or may be joined from multiple separate pieces. Additionally, one or more portions of the staple (502) (e.g., the base or portions thereof, the legs or portions thereof, etc.) may be rigid, while one or more other portions of the staple (502) may be flexible.

Figure 6A:
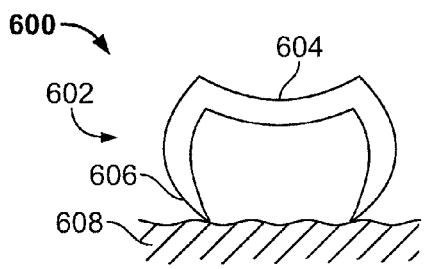
FIGS. 6A, 6B, 7A, 7B and 8 illustrate different variations of the devices described here, where the device comprises a staple.
Figure 6B:
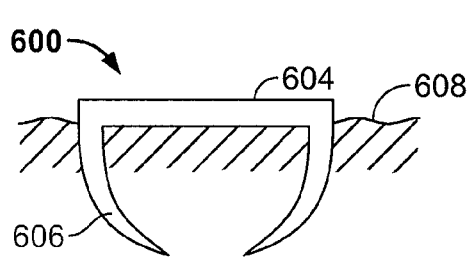
Figure 7A:
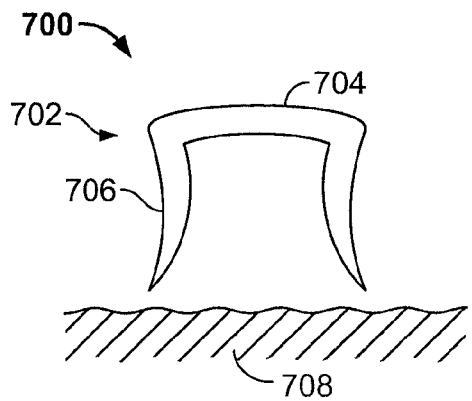
Figure 7B:
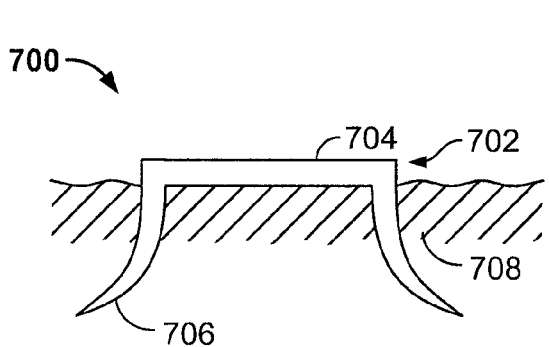

Generally, legs (506) may be configured to puncture tonsillar tissue. In some variations, one or more legs (506) may comprise one or more barbs, prongs, notches, or other structures that help to hold legs (506) in place once implanted in tissue. Additionally, while shown in FIG. 5 as being straight, legs (506) need not be. Indeed, one or more legs (506) may be curved. In some of these variations, one or more legs (506) may be curved inwardly. FIGS. 6A and 6B illustrate one such variation of tissue-piercing device (600) comprising staple (602) having base (604) and inwardly-curved legs (606). To implant staple (602) in tissue, base (604) may be flexed and the ends of legs (606) may be placed adjacent tonsillar tissue (608), as shown in FIG. 6A. The base (604) may then be unflexed, which may in turn drive legs (606) into tonsillar tissue (608), as shown in FIG. 6B. Once implanted into tissue (608), the curved legs (606) may help to prevent staple (602) from being pulled out of tissue (608). Additionally, curved legs (606) may reduce the overall depth of penetration of staple (602), which may reduce the chance of staple (602) damaging one or more sensitive structures, such as the glossopharyngeal nerve. Similarly, FIGS. 7A and 7B illustrate another variation of tissue-piercing device (700) comprising a staple (702) with base (704) and outwardly-curved legs (706). To implant staple (702) into tissue (708), base may be flexed and the ends of legs (706) may be placed adjacent tissue (708), as shown in FIG. 7A. The base (704) may then be unflexed, which may in turn drive legs (706) into tissue (708), as shown in FIG. 7B.

Figure 8:
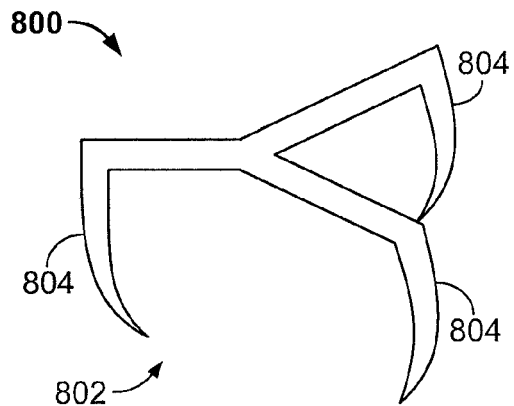

While shown in FIGS. 5, 6A, 6B, 7A and 7B as having two legs, a staple may have any suitable number of legs (e.g., two, three, four, or five or more). For example, FIG. 8 shows one variation of tissue-piercing device (800) comprising staple (802) having three legs (804). While all three legs (804) are shown in FIG. 8 as being inwardly curved, each leg (804) may be straight, outwardly curved, or have some alternate configuration. Each leg (804) may have the same configuration, or may have different configurations.

Clips

Some variations of the devices described here may comprise one or more clips. Generally, each clip comprises a surface member and one or more anchoring members, and is configured to attach to tonsillar tissue by at least partially implanting one or more anchoring members into tissue. This may be achieved by pushing a clip against tonsillar tissue such that the anchoring members are driven into tissue. In some variations, one or more portions of the clip may be configured to release one or more drugs. When the clip is configured to release one or more drugs, it may do so in any suitable manner, such as those described in more detail below. Additionally, the clip may or may not be configured to biodegrade, bioerode, or otherwise break down.

Figure 9A:
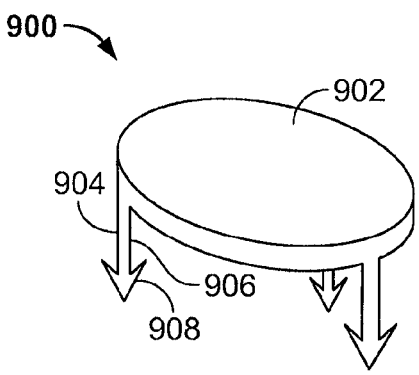
FIGS. 9A and 9B illustrate a perspective view and a side view, respectively, of one variation of a device comprising a clip.
Figure 9B:
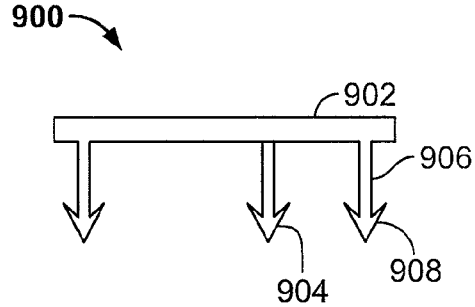

FIGS. 9A and 9B show a perspective view and a side view, respectively, of one such variation of clip (900). Shown there is surface member (902) and anchoring members (904). Surface member (902) is generally configured to remain at or above a tonsillar tissue surface while anchoring members (904) may pierce, puncture or otherwise penetrate tonsillar tissue to attach clip (900) thereto. Surface member (902) may shield otherwise exposed tonsillar tissue against stimuli, forces, or materials that may otherwise come into contact with the tonsillar tissue. While shown in FIGS. 9A and 9B as being a circular plate, surface member (902) may be any suitable size or shape. In some variations, surface member (902) may be oval, squared, rectangular, triangular, polygonal, or may have an irregular shape. Additionally, while shown in FIGS. 9A and 9B as being flat, surface member (902) need not be. Indeed, surface member (902) may comprise one or more ridges, waves, bumps, uneven surfaces, or the like. Surface member (902) may be rigid, or may be flexible. In some variations, surface member (902) may have one or more rigid portions and one or more flexible portions.

Anchoring members (904) may have any suitable size, shape, and configuration of elements. As shown in FIGS. 9A and 9B, anchoring elements (904) may comprise struts (906) with barbs (908). Similarly, anchoring member (904) may comprise any suitable structure, including, but not limited to, struts, barbs, spikes, hooks, curved legs, combinations thereof and the like. FIGS. 10A and 10B show a top perspective view and bottom perspective view, respectively, of one such variation of clip (1000). Shown there is surface member (1002) and anchoring members (1004) comprising v-shaped barbs (1006). Also shown there is reinforcement member (1008), which may be any suitable structure (e.g., a bar, rod, plate, etc.) capable of providing structural reinforcement to at least a portion of surface member (1002). FIG. 11A illustrates another such variation of clip (1100). Shown there is surface member (1102) and anchoring members (1104) comprising curved legs (1106). Curved legs may help anchor clip (1100) to tissue while reducing the depth at which the anchoring member (1104) penetrate. While shown in FIG. 11A as being curved outward, curved legs (1106) may also be curved inward. Additionally, a clip may have a combination of the anchoring devices described here. FIG. 11B illustrates one such variation of clip (1108) comprising surface member (1110), curved legs (1112) and barbed strut (1114).

The surface member and anchor members may be made of a single piece of material, but need not be. Indeed, in some variations one or more sutures or tissue-piercing devices described above may be used to anchor a surface member to tissue. In some of these variations, the suture (or a needle attached thereto) or tissue-piercing device may be used to puncture one or more portions of the surface member. In other variations, the surface member may comprise one or more apertures through which a suture or tissue-piercing device may pass to anchor the surface member to tonsillar tissue. FIG. 12 shows one such variation of clip (1200). Shown there is surface member (1202) comprising apertures (1204). Also shown there is staple (1206) with legs (1208) passing through two of the apertures (1204).

Tissue-Restricting Devices

In some variations of the devices described here, the devices may be configured to stretch, immobilize, tension, reposition, or otherwise resist changes in tonsillar tissue. FIGS. 13A-13D illustrate one such device (1300). Shown in FIG. 13A is a perspective view of device (1300) comprising body member (1302) and anchors (1304). FIG. 13C shows a side view of device (1300) implanted in tonsillar tissue (1306), such that anchors (1304) at least partially penetrate the tonsillar tissue (1306) at penetration sites (1308). FIG. 13D shows a perspective view of device (1300) implanted between the palatoglossal (1314) and palatopharyngeal (1316) arches.

Once implanted into an area of tonsillar tissue (1306), device (1300) may act to restrict movement of that tissue. Generally, body member (1302) is made of a material that is capable of flexing or bending from an original shape when subjected to one or more forces or stimuli, but has a tendency to return to its original shape when the force or stimuli is removed. The original shape of the body member (1302) may be flat, or may comprise one or more curves or bends. Certain actions (i.e. swallowing) may cause tonsillar tissue to move, shift, or otherwise reconfigure, which under certain circumstances (e.g., following a tonsillectomy) may cause pain or discomfort. This movement may cause tonsillar tissue (1306) between penetration sites (1308) move toward each other, as indicated by arrows (1310) in FIG. 13C, which may in turn cause body member (1302) to bend or flex. The body member's (1302) tendency to return to its original shape may resist this bending or flexing. This resistance may in turn cause the device (1300) to provide one or more forces (1312) to the tonsillar tissue (1306) at penetration sites (1308). These forces (1312) may help to keep the tonsillar tissue (1306) stretched, and may prevent the tonsillar tissue (1306) from otherwise moving. This, in turn, may help to minimize pain or discomfort experienced by a patient.

Additionally, the tendency of body member (1302) to return to its original shape may help to keep device (1300) implanted in tonsillar tissue (1306). Before the anchors (1304) of device (1300) are inserted into tonsillar tissue (1306), the body member (1302) may be slightly flexed or bent, as shown in FIG. 13B. The anchors (1304) may then be inserted into tissue (1306), and the tendency of body member (1302) to return to its original shape may bias anchors (1304) into the tonsillar tissue (1306). This may cause the device to continually apply one or more forces to tissue, which may thereby hold the tonsillar tissue (1306) in a stretched configuration.

Figure 14:
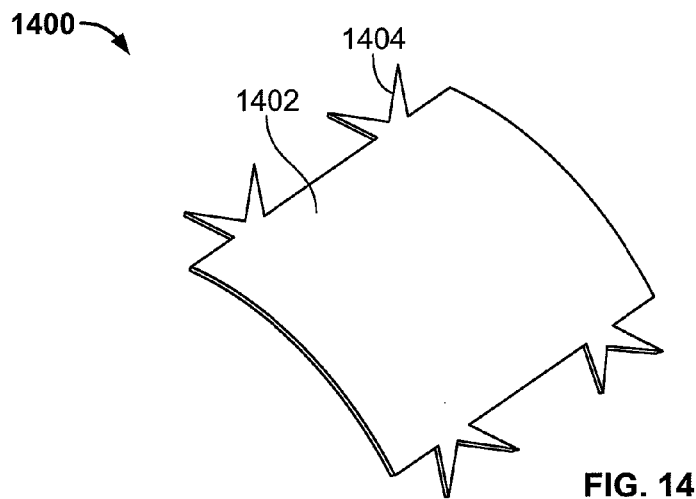

While shown in FIGS. 13A-13D as being rectangular in shape, body member (1302) may have any suitable dimensions or shape. For example, FIG. 14 shows one such variation of device (1400) comprising a square-shaped body member (1402) and anchors (1404). Other suitable body member shapes include, but are not limited to, circles, ovals, triangles, polygons, shapes with irregular geometry, and the like. While shown in both FIGS. 13A-13C as having anchors (1304), device (1300) need not. In variations that do include anchors (1304), device (1300) may comprise any number of anchors (e.g., one, two, three, four, five, six, or seven or more). Each anchor (1304) may have any suitable size, shape, or dimensions. In some variations, such as that shown in FIGS. 13A-13C, an anchor may comprise a single spear. In other variations, such as that shown in FIG. 14, an anchor may comprise two or more spears. In still other variations, an anchor may comprise one or more barbs, spears, thorns, hooks, or other structures capable of affixing a body member to tissue.

Figure 15:
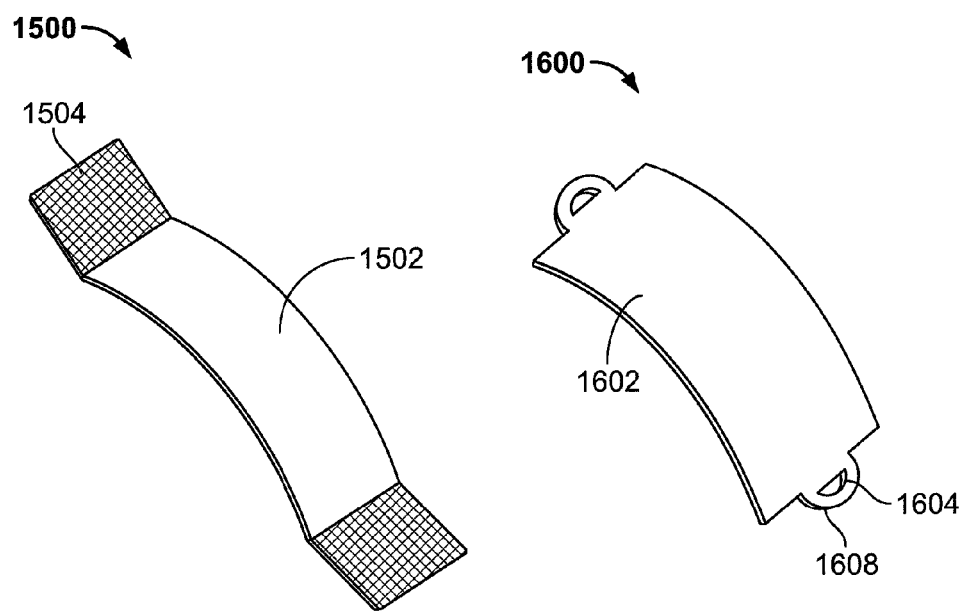

In variations that do not include an anchor, the body member may be connected to tonsillar tissue in any suitable way. FIG. 15 shows one such variation of device (1500), comprising body member (1502) and strips (1504). Generally, strips (1504) are attached to tissue to anchor device (1500) against tonsillar tissue (not shown). This can be done in any suitable manner. In some variations, one or more strips (1504) may be sutured into or against tissue. In other variations, one or more strips (1504) may comprise one or more adhesives that connect the strips (1504) to tissue. In still other variations, one or more of the tissue-piercing devices described above may be inserted at least partially through one or more strips (1504) to anchor the strips to tissue. Each strip (1504) may be made from any suitable material, such as, for example, a woven or non-woven mesh.

Figure 16A:
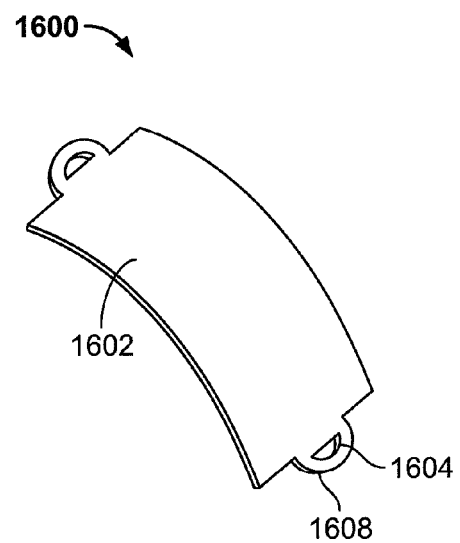
Figure 16B:
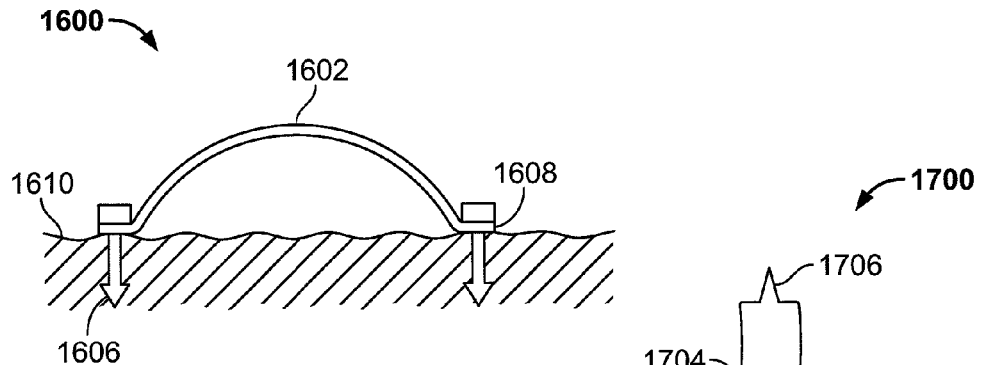

FIGS. 16A and 16B illustrate another suitable variation of device (1600) comprising body member (1602). FIG. 16A shows a perspective view of body member (1602), including one or more apertures (1604). Apertures (1604) may be configured such that at least a portion of one or more anchoring devices (1606) may pass therethrough to hold the ends (1608) of body member (1602) against tonsillar tissue (1610), as shown in a side view in FIG. 16B. The anchoring devices (1606) may be any suitable structure, such as, for example, one or more of the tissue-piercing devices described above. Body member (1602) may comprise any number of apertures (1604) (e.g., one, two, three, four, five, or six or more), but the number of anchoring devices (1606) used need not match the number of apertures (1604). In some instances, one or more apertures (1604) may go unfilled, or an individual anchoring device (1606) (e.g., a two-pronged staple) may pass through multiple apertures (1604).

Figure 17:
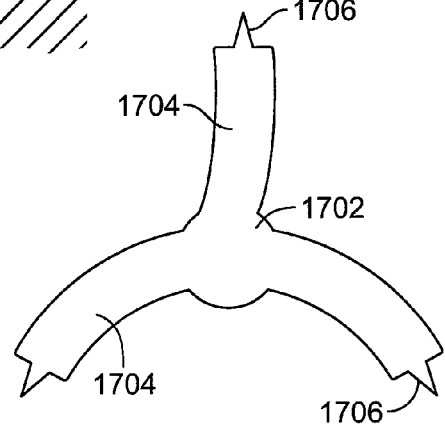

While the variations shown in FIGS. 13A-16B are configured to apply force to tonsillar tissue in two directions, the body members may be configured to apply force in any number of directions. FIG. 17 illustrates one such variation of device (1700) in which body member (1702) is configured to apply force to tonsillar tissue (not shown) in three directions. As shown there, body member (1702) comprises three arms (1704), each having an anchor (1706). When implanted in tissue (not shown), each arm may be capable of exerting one or more forces to tonsillar tissue. While shown in FIG. 17 as all having anchors (1706), each arm may be attached to tissue in any suitable manner described above. Additionally, body member (1702) may have any suitable number of arms (e.g., one, two, three, four, or five or more).

Figure 18A:
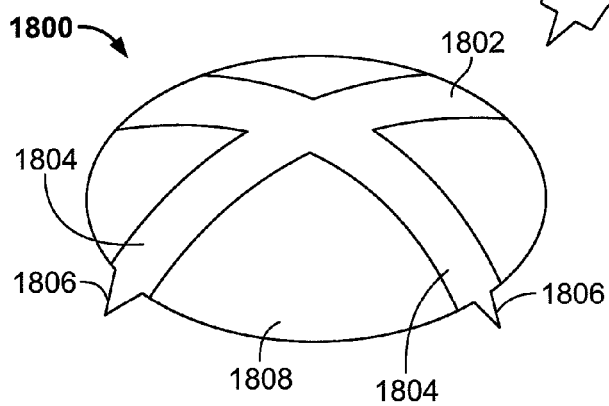
Figure 18B:
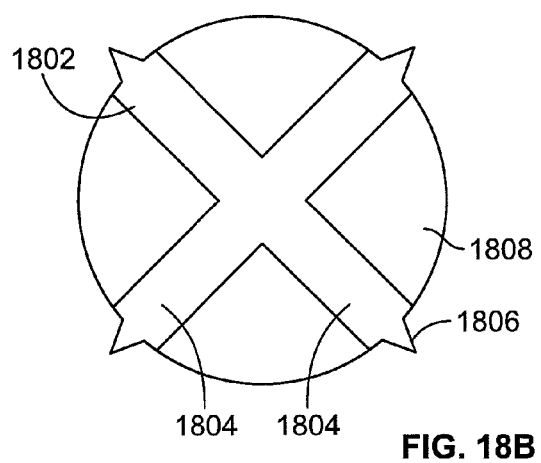

FIGS. 18A and 18B show another suitable variation of device (1800). Shown there is body member (1802) comprising arms (1804), anchors (1806), and flaps (1808). While shown there as having four arms (1804), body member (1802) may have any suitable number of arms, and each arm may be attached to tissue in any suitable manner, as described in more detail above. Additionally, flaps (1808) may span between adjacent arms (1804), and may act to cover tissue. In this way, device (1800) may help to protect exposed tonsillar tissue from contact with one or more materials that may irritate the tissue or otherwise cause pain to a patient. Flaps (1808) may be made from any suitable material, including, but not limited to one or more meshes, films, or sheets.

Figure 25A:
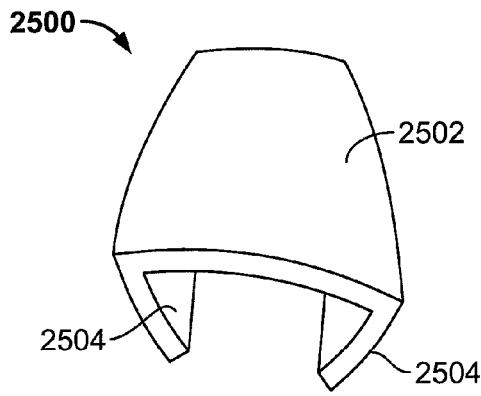
FIGS. 25A-25D illustrate depictions of a variation of a device that is configured to hold or restrain tissue.
Figure 25B:
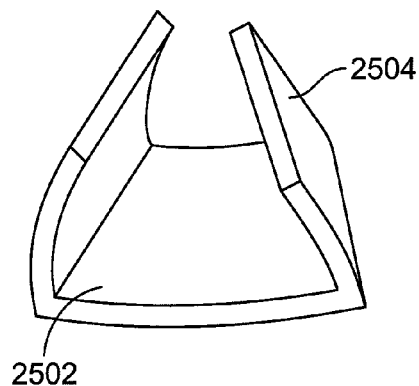
Figure 25C:
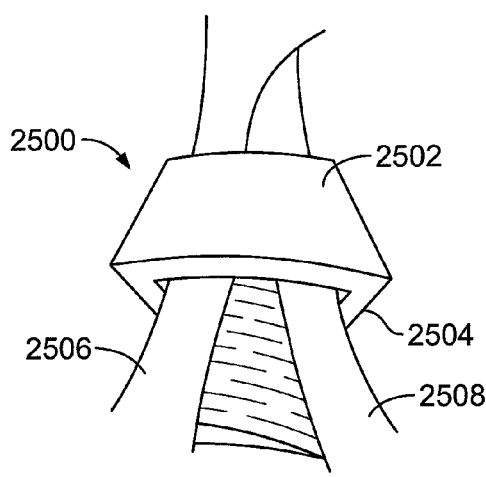

In still other variations, one or more devices may be configured to compress tissue or pull two or more areas of tissue toward each other. For example, FIGS. 25A-25D illustrate one variation of device (2500). FIGS. 25A and 25B illustrate top and bottom perspective views respectively of device (2500) comprising base portion (2502) and wings (2504). Device (2500) may be configured such that it may hold tissue between wings (2504). For example, device (2500) may be placed in the throat such that device (2500) holds the palatoglossal (2506) and palatopharyngeal (2508) arches between wings (2504), as shown in FIG. 25C. In these variations device (2500) may act to bring or hold one or more portions of the palatoglossal (2506) and palatopharyngeal (2508) arches in closer approximation. In some variations, device (2500) may further serve to hold one or more additional device (not shown) between the arches.

Figure 25D:
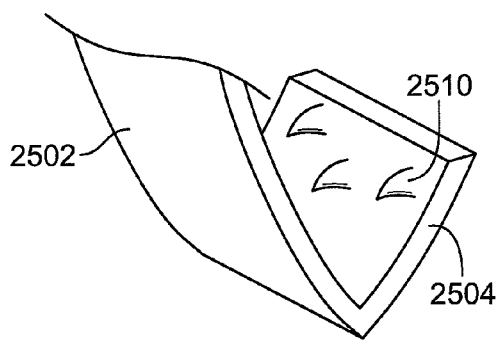

Additionally, in some variations, device (2500) may comprise one or more additional structures to help hold device (2500) in place relative to tissue. For example, some variations wings (2504) of device (2500) may comprise one or more barbs (2510), as illustrated in FIG. 25D. These barbs may anchor into or otherwise engage surrounding tissue to help hold device (2500) in place. Although shown in FIG. 25D as comprising barbs (2510), device may comprise any structure suitable for improving engagement between device (2500) and tissue, such as, for example, hooks, spikes, prongs, or the like.

Space-Filling Implants

Figure 19A:
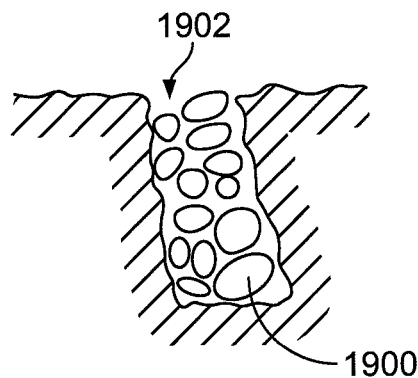
FIGS. 19A, 19B and 20 are illustrative depictions of variations of devices described here, where the device comprises a plurality of space-filling implants.
Figure 19B:
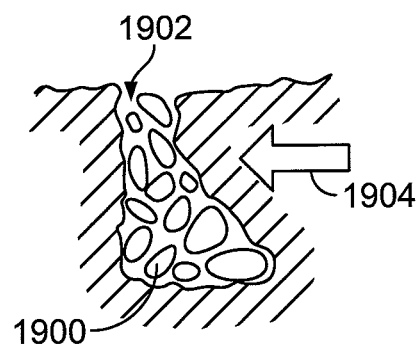

In some variations, the devices comprise one or more space-filling implants. These space-filling implants may be any suitable structure, such as, for example, pellets, seeds, beads, capsules, microspheres, microcapsules, combinations thereof or the like. Generally, a plurality of these space-filling implants may be used to at least partially fill one or more cavities, chambers, or spaces inside of a tissue. For example, FIGS. 19A and 19B show a plurality of beads (1900) placed into space (1902). When placed in space (1902), as shown in FIG. 19A, the plurality of beads (1900) may self-assemble to conform to the contours of space (1902). This self-assembly allows the space-filling implants to fit within spaces (1902) of varying sizes and shapes. Additionally, one or more gels or foams, such as those described in more detail below, may be used to fill in any gaps between space-filling implants.

Additionally, when one or more forces (1904) or other stimuli cause the dimensions of space (1902) to change, the plurality of beads (1900) may adjust to conform to this change, as shown in FIG. 19B. In some variations, however, the space-filling implants may resist changes to the space (1902) in which they are placed. In some variations, the space-filling implants may adhere to each other once implanted, such that the space-filling implants are joined or otherwise attached together after their initial self-assembly. This adherence may be achieved in any suitable manner, such as, for example, covering the space-filling implants with one or more adhesive coatings (e.g., coatings of fibrin glue, cyanoacrylate glue, or the like), or providing one or more stimuli (e.g., heat, light, etc.) that cause adjoining space-filling implants to fuse together. Once two space-filling implants become joined or attached, they may resist movement relative to each other. Thus, when a force or stimulus would otherwise cause the shape or size of space change, the attached space-filling implants may resist this change.

While shown in FIGS. 19A and 19B as being an oval-shaped bead (1900), each space-filling implant may have any suitable shape. For example, an individual space-filling implant may be spherical, box-shaped, conical, frustoconical, rod-like, pyramidal, irregularly shaped, combinations thereof, or the like. Additionally, one space-filling implant may or may not have the same shape and dimensions as another space-filling implant. The space-filling implants may or may not be configured to release one or more drugs, as described in more detail below, and may or may not be configured to biodegrade, bioerode, or otherwise break down.

Figure 20:
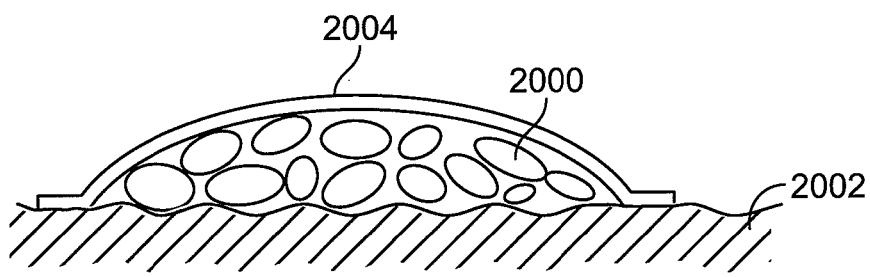

The space-filling implants described here may be placed in any suitable space in or around tonsillar tissue, and may be delivered via any suitable structure (e.g., a funnel, needle, hypotube, cannula, or other tube-like structure). In some instances, this space may be naturally occurring (e.g., a gap between two tissues). In other instances, this space may be artificially formed. For example, one or more channels or gaps may be formed during a tonsil procedure. Alternatively, one or more spaces may be created (e.g., by inserting a needle, trocar, or other suitable device into tissue) for the purpose of receiving a plurality of space-filling implants. In other variations, a plurality of space-filling implants may at least partially fill one or more cavities, chambers, or other spaces disposed inside of one the other devices described above. In still other variations, space-filling implants adhere to tissue, and are placed adjacent a tissue surface. In yet other variations, one or more patches, meshes, films, sheets, or the like may used to hold a plurality of space-filling implants in place against tissue. FIG. 20 illustrates one such variation in which space-filling beads (2000) are held in place against tonsillar tissue (2002) by a patch (2004). Patch (2004) may be attached or joined to tissue in any suitable manner, such as those described below.

In some variations, one or more of space-filling implants comprise a capsule or other structure that has one or more cavities or spaces formed therein. In these variations, the space-filling implant may burst or otherwise break when subjected to a certain force or stimulus (e.g., heat, light, pH change, chemicals, etc.). One or more solutions or substances (e.g., drug-containing solutions, adhesives, etc.) may be placed in these structures, such that the solution or substance is released when the space-filling implant breaks. For example, one or more of the space-filling beads (2000) shown in FIG. 20 may comprise a cavity (not shown) which holds an anesthetic or painkiller therein. When one or more forces or stimuli are applied to patch (2004), such as, for example, compressive forces that may occur when swallowing food, these forces or stimuli may cause one or more space-filling beads (2000) to rupture. This may release an amount of anesthetic or painkiller, which may reduce the sensation of pain in the tonsillar tissue.

In variations where one or more space-filling implants comprise a capsule or other cavity-containing structure, these space-filling implants may be configured to break or rupture at different times. In some variations, devices with different dimensions may rupture under different forces. For example, a device with a thicker wall surrounding a cavity may require a greater force to rupture than a device with a thinner wall surrounding the cavity. In variations where the space-filling implants are configured to biodegrade, bioerode, or otherwise break down, the space-filling implants may become more susceptible to rupturing over time. As such, by providing space-filling implants with different degradation times, some space-filling implants may rupture at earlier times than others. Overall, the space-filling implants may be configured to break or rupture at different times over the span of a treatment regimen.

In other variations, the space-filing implants may comprise a capsule that is configured to break or dissolve to release a material that solidifies after release. For example, in some variations different space-filling implants may comprise different components of a fibrin glue. When the capsules break, the components of the fibrin glue may mix to form a solid fibrin matrix, which in turn may adhere to surrounding tissue. Generally, a fibrin clot may be formed by mixing fibrinogen and thrombin in an aqueous environment, as the thrombin polymerizes the fibrinogen into a polymer matrix. Thus, in these variations, some capsules may contain a thrombin solution, while other capsules contain a fibrinogen solution. When the capsules break or dissolve, these components may join to form a polymerized fibrin matrix. It should be appreciated that the fibrinogen and thrombin solutions may comprise one or more clotting factors or other elements (calcium chloride) that may aid in the fibrin polymerization process, and may also comprise one or more drugs or agents that may be released from the resulting fibrin matrix.

In still other variations, one or more space-filling implants may be expandable. These space-filling implants may be any suitable expandable structure, such as, for example, an inflatable structure (e.g., a balloon) or a swellable implant. The expandable space-filling implants may be delivered to one or more spaces, such as those described above, in either an expanded or an unexpanded form. When delivered in an unexpanded from, the expandable space-filling implants may expand in response to one or more forces or stimuli. These forces or stimuli may or may not be naturally provided by the body. For example, when a space-filling implant comprises one or more swellable materials, the space-filling implant may expand as it comes into contact with saliva or other fluids introduced to tonsillar tissue. When the space-filling implant comprises a balloon or other inflatable structure, the balloon may be inflated after delivery to the tonsillar tissues. In some variations, the balloon may be filled with a drug-containing solution, and may be configured to elute one or more drugs over a period of time. In other variations, the balloon may comprise one or more elements (e.g., hooks, barbs, or the like) that may anchor the balloon to one or more areas of tonsillar tissue. Additionally, when one or more expandable space-filling implants expand in or around a space in the tonsillar tissues, the space-filling implants may exert one or more forces on the surrounding tissue, and in some instances may dilate or otherwise reconfigure surrounding tonsillar tissue.

Foams and Gels

In some variations, one or more gels or foams may be administered to one or more portions of the tonsillar tissue. Gels or foams may be administered to tonsillar tissue during or following a tonsil procedure. Gels or foams may provide one or more beneficial functions. In some variations, the gels or foams may deliver one or more drugs to surrounding tissues, as will be described in more detail below. In other variations, the gels or foams may help to seal off or otherwise shield exposed tonsillar tissue or exposed tissue of the tonsillar fossa from external stimuli, such as acidic compounds or other aggravating chemicals that may be ingested while eating or drinking, or abrasive forces or temperature changes caused by ingesting food or liquids.

Any suitable gel or foam may be used. In some variations, the gels or foams may be biodegradable, bioabsorbable, bioerodible, dissolvable, or otherwise configured to break down. Gels may be made from any colloidal system in which a porous network of small particles, which may or may not be connected, spans the volume of a liquid medium. Foams may be formed by trapping one or more gas bubbles in a liquid or solid. In some variations, one or more gels or foams may naturally adhere to tissue. For example, when a gel or foam is made from chitosan, chitin, polyvinylpyrrolidone (PVP), polyvinyl alcohol (PVA), fibrin glue, or similar materials, that gel or foam may adhere to tissue.

In instances where one or more gels or foams are administered to tissue, they may be administered in any suitable way. In some variations, one or more gels or foams may be placed in one or more holes, channels, gaps, or other spaces inside of tonsillar tissue. These spaces may be naturally occurring or artificially formed. In other instances, one or more gels or foams may be used to cover or coat one or more tissue surfaces. In some of these variations, the gel or foam may naturally adhere to a tissue surface, as noted above. In other variations, one or more structures may be used to hold the gels or foams in place against the tissue. Indeed, in some of these variations, one or more patches, films, sheets, or meshes, as described in more detail below, may be used to hold one or more gels or foams against tissue. In these variations, the patch, film, sheet, or mesh may be anchored or otherwise attached to tissue, and the one or more gels or foams may be placed beneath the patch, film, sheet, or mesh. Any suitable patch, film, sheet, or mesh may be used, such as those described herein. In instances where the mucosal flap is sutured over the exposed tonsillar bed, one or more gels or foams may be placed beneath the mucosal flap.

In other variations, one or more gels or foams may be capable of solidifying upon delivery. The gels or foams may solidify in response to one or more stimuli (e.g., heat, energy, light, changes in pH, moisture, chemicals or biological materials, etc.), or may solidify naturally upon delivery to tonsillar tissue. In some of these variations, the gel or foams may delivered to one or more spaces in or around the tonsillar tissue, at which point the gel or foam may solidify. When the gel or foam contains one or more drugs, the gel or foam may be used to create one or more solid drug-releasing boluses.

Additionally, one or more gels or foams may be used in conjunction with one or more of the devices described here (e.g., tissue-piercing devices, tissue-restriction devices, clips, space-filling implants, or a combination thereof). In some variations, one or more gels or foams may be used to at least partially coat one of the devices. In other variations, one or more gels or foams may be used to fill one or more spaces, cavities or reservoirs within one of the devices.

Patches, Sheets, Films, and Meshes

In some variations one or more patches, sheets, films, meshes, or a combination thereof may be placed in, on, or around the tonsillar tissue. Any of these devices may or may not be configured to deliver one or more drugs to the tonsillar tissue. When configured to deliver one or more drugs, the patches, sheets, films, or meshes may release drug in any suitable manner as described below. Additionally, one or more portions of these devices may be configured to biodegrade, bioerode, or otherwise break down.

Generally, one or more patches, sheets, films, meshes, or a combination thereof may be applied to tonsillar tissue. In some instances, one or more of these devices may be at least partially implanted in tissue. In other instances, one or more of these devices may be used to cover one or more tissue surfaces. When these devices are used to cover one or more tissue surfaces, the patches, sheets, films or meshes may help to shield the tonsillar tissue from one or more stimuli or chemicals that may irritate tonsillar tissue. In some instances, the patches, sheets, films, or meshes may entirely or partially seal some or all of a portion of tonsillar tissue from outside stimuli or chemicals. In other instances, the patches, sheets, films or meshes may act as a temporary haemostatic barrier. Additionally, these patches, sheets, films or meshes may be used to hold one or more additional devices against tonsillar tissue. In other variations, the patches, sheets, films, or meshes may be configured such that blood, or one or more components of blood, may pass through at least a portion of the device.

These devices may be attached to tonsillar tissue in any suitable manner. In some variations, one or more portions of the device may naturally adhere to tissue. For example, when a film or sheet is made from a polymer such as chitosan, chitin, PVP, PVA, or the like, the film or sheet may adhere to tissue. For example, sucralfate may be used to help connect one or more portions of the device to tissue. In other instances, one or more biocompatible adhesives (e.g., a fibrin glue or a cyanoacrylate glue) may be used to connect one or more portions of the device to tissue. In still other instances, one or more sutures or the tissue-piercing devices may be used to anchor one or more portions of the device to tissue. In yet other instances, one or more additional patches, films, sheets, or meshes may overlay the device to hold it in place. In still other instances, one or more of the clips or tissue-restricting devices described above may be used to anchor one or more portions of the device to tissue.

Any suitable patch, film, sheet, or mesh may be administered to the tonsillar tissue. When a mesh is used, the mesh may be woven or non-woven, and may have any suitable pore size. In some variations, the mesh comprises a pore size sufficient to allow for tissue ingrowth. Indeed, any of the patches, sheets, or meshes may be configured for tissue ingrowth. For example, a patch, film, sheet, or mesh may comprise one or more roughened or porous surfaces that may help to initiate tissue ingrowth.

When a film is applied to tissue, the film may be preformed or may be formed after administration to tissue. In variations when the film is formed upon administration, a gel or foam, such as those described above, or some other solidifying material may be administered to the tonsillar tissue. In some variations, the gel or foam naturally cures into a film when placed against tonsillar tissue. In other variations, the gel or foam cures upon application of one or more stimuli thereto. Examples of suitable stimuli include, but are not limited to heat, light, electricity, moisture, chemicals, biological materials (e.g., proteins, enzymes, and the like), and changes in pH. In some variations, a layer of fibrin glue may be applied to a tissue surface to form a polymerized fibrin sheet thereon. When a sheet is applied to tonsillar tissue, the sheet may be made from any suitable material, such as those described below.

Figure 26A:
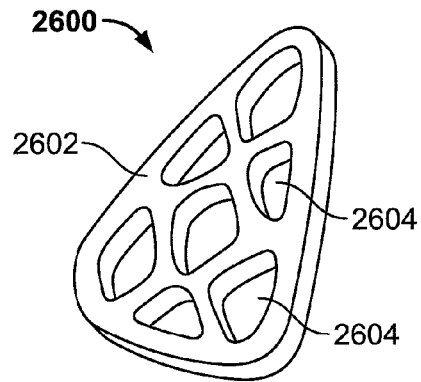
FIGS. 26A and 26B illustrate a variation of a device comprising a patch.
Figure 26B:
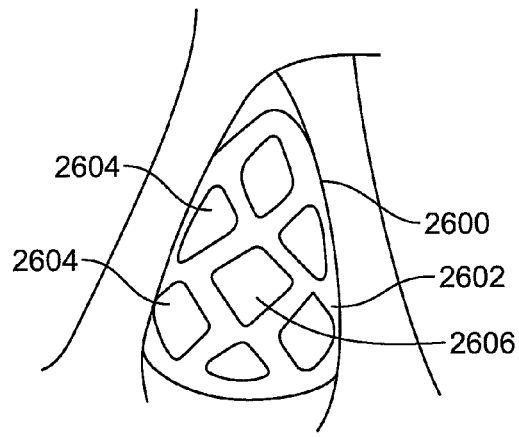

When tonsils are removed during a tonsillectomy, one or more clots may form on or in the tonsillar beds. In some instances, a large scab may dislodge from tonsillar tissue during recovery from a tonsil procedure, which may result in a potentially problematic bleeding episode. To help prevent such a bleeding episode, it may be desirable to minimize the size of clots that may form on tonsillar tissue. As such, it may be desirable for a patch or sheet to comprise one or more apertures or cells passing therethrough to help regulate the size of clots formed. For example, FIGS. 26A and 26B illustrate one variation of patch (2600). Shown in FIG. 26A is patch (2600), which comprises a frame (2602) and a plurality of cells (2604) defined thereby. The patch (2600) may be placed over and attached to the tonsillar bed (2606) or other tonsillar tissue during or following a tonsil procedure, as shown in FIG. 26B. When placed against tissue, blood may pool in cells (2604), and may form a plurality of smaller scabs (not shown). These smaller scabs may reduce the likelihood that a bleeding episode will occur. It should be appreciated that cells (2604) may be any suitable size or shape, and that patch (2600) may have a thickness sufficient to allow for pooling of blood in cells (2604).

Drug Delivery

Any of the devices described here may be used to deliver one or more drugs. Each device described here may be configured to release any suitable number of drugs over any suitable period or periods of time. The number of drug-releasing devices, the selection of drugs, the timing of delivery, and the overall amount of drug or drugs released may be determined by the intended treatment plan, and may be further fine-tuned to the meet the specific needs of an individual patient. Each drug delivered should be released at a rate that provides a patient with a healthy, safe, and effective dosage and should be administered at an overall dosage that is also healthy, safe, and effective.

The devices described here may deliver one or more drugs in any number of ways. In some variations, at least a portion of the device itself incorporates one or more drugs. In some instances, the drug may diffuse out of or may otherwise be released from the device over time. In other instances, the device may comprise one or more cavities, channels, pockets or other space from which a drug or drug-containing material may be released. In still other variations, the device may comprise one or more drug-eluting layers, boluses or reservoirs disposed on one or more surfaces of the device.

Any suitable device or portions thereof may be configured to release one or more drugs to tonsillar tissue. In some variations, one or more drugs may be incorporated into one or more portions of the device's body. Each drug may be incorporated into the entire body, or may only be incorporated into one or more portions of the body. For example, in variations where the device comprises a staple with two legs, as described above, a first drug may be incorporated into the first leg, while a second drug may be incorporated into the second leg. In some instances, the one or more drugs may diffuse out of the device body. In variations where one or more portions of the device is biodegradable, bioerodible, or otherwise configured to break down, the one or more drugs may be released as these portions degrade or erode.

In other variations, the body of the device may comprise one or more cavities, channels, pores, pockets or other spaces that may hold one or more drugs or drug-containing materials. The spaces may hold one or more drugs, one or more drug-containing solutions, foams, powders, solids, gels, or a combination thereof. In some variations, one or more drugs may diffuse out of the spaces through the device body. In other variations, the drugs or drug-containing materials may exit the device via one or more pores or passageways in the body of the device. In variations where one or more portions of the device is biodegradable, bioerodible, or otherwise configured to break down, one or more of the spaces may become exposed to tissue as these portions degrade or erode. In these instances, one or more drugs or drug-containing materials may be released from the device when the space becomes exposed to tissue.

In still other variations, one or more surfaces of a device may comprise one or more drug-releasing layers or boluses disposed thereon. The drug-releasing layers or boluses may be made of any suitable biocompatible material that is capable of releasing a drug over a period of time, and may be configured in any suitable way. Each device may comprise any number of drug-releasing layers or boluses (e.g., zero, one, two, three, four or more). Each drug-releasing layer may coat or cover the entire surface of the device, or may only cover one or more selected portions of the device. Additionally, one drug-releasing layer may be at least partially disposed over one or more additional drug-releasing layers.

Overall, the device may be configured to release one or more drugs over a predetermined period of time. This period of time may be on the order of hours, on the order of days, or on the order of weeks. This period of drug delivery will likely be determined with consideration of the nature and amount of the drug or drugs to be released as well as the intended treatment regimen. For example, when the device is used to treat one or more symptoms of a tonsil procedure, the period may be between less than about a day, between about 1 day to about 21 days, between about 1 day to about 18 days, between about 1 day to about 15 days, between about 1 day to about 12 days, between about 1 to about 9 days, between about 1 to about 7 days, between about 1 to about 5 days, between about 1 to about 3 days, between about 3 days to about 21 days, between about 3 days to about 18 days, between about 3 days to about 15 days, between about 3 days to about 12 days, between about 3 to about 9 days, between about 3 to about 7 days, between about 3 to about 5 days, between about 5 days to about 21 days, between about 5 days to about 18 days, between about 5 days to about 15 days, between about 5 days to about 12 days, between about 5 to about 9 days, between about 5 to about 7 days, between about 7 days to about 21 days, between about 7 days to about 18 days, between about 7 days to about 15 days, between about 7 days to about 12 days, between about 7 to about 9 days, between about 9 days to about 21 days, between about 9 days to about 18 days, between about 9 days to about 15 days, between about 9 days to about 12 days, between about 12 days to about 21 days, between about 12 days to about 18 days, between about 12 days to about 15 days, between about 15 days to about 21 days, between about 15 days to about 18 days, or between about 18 days to about 21 days. As will be described in more detail below, this period may not begin immediately upon implantation or administration of the device.

Drugs may be released at a constant rate from the device, but need not be. Indeed, the devices may be configured with any suitable release rate profile. In some variations, the daily amount of drug released may decrease over time. For example, a device may release a certain amount of drug for a first period of time (e.g., one day), then may release a second amount of drug for a second period of time. Similarly, the amount of drug delivered may change any number of times during a span of time. The amount of drug released may decrease over time, or may increase over time, or may increase over one span of time and decrease over a different span of time. Furthermore, in some variations a device may comprise multiple drug eluting layers, and each layer may be configured to have a different and specific release profile. Of course, it should be understood that each layer may comprise, contain, include, or be configured to release one or more drug or agent therefrom. Each layer may comprise, contain, include, or be configured to release the same or a different drug or agent therefrom. Similarly, the device body may additionally comprise a drug, and the device body may provide a different release profile from those of one or more drug eluting layers.

In still further variations, the device may comprise one or more barrier layers. These layers may or may not release one or more drugs, and may delay the release of one or more drugs from one or more drug releasing layers or from the device itself. The barrier layer may or may not be a bulk-eroding polymer, or may or may not be a surface-eroding polymer. In some variations, the barrier layer may prevent the passage of drug therethrough. In these variations, the barrier layer may provide a time during which no drug is released from at least a portion of a drug releasing layer or from at least a portion of the device. Once the barrier layer has sufficiently degraded or otherwise eroded, drug release may begin or resume. In other variations, the barrier layer may allow some amount drug to pass therethrough. In some of these variations, the amount of drug that passes through barrier layer may be less than that which would be released from the drug releasing layer in the absence of the barrier layer. The barrier layer thus may provide a period during which a smaller amount of drug is released from at least a portion of the drug releasing layer. Once the barrier layer has sufficiently degraded or otherwise eroded, the amount of drug released from the device may increase.

These aforementioned drug-delivery variations, and combinations thereof, may allow the device to provide a variable drug release profile, or provide bursts, either initial or delayed, in addition to the device's baseline release profile. Additionally, these variations may allow the device to provide different drug release profiles that are separated in time. For example, the device may comprise two drug releasing layers separated by a barrier layer. The outer drug releasing layer may release an initial amount of drug over an initial period of time, and may follow any suitable drug release profile. The barrier layer may then degrade or erode over a certain period of time, during which some or no drug is released from a second drug releasing layer. Once this degradation has substantially finished, the second drug releasing layer may then release a second amount of drug over a second period of time, and this release may also follow any suitable drug release profile. Each drug releasing layer may release any suitable amount of any suitable drug over any suitable amount of time, as described above.

Additionally, one or more release rate modifiers may also be used. The release rate modifier may be any suitable biocompatible material that serves to alter the rate at which a drug is released from the device. In some variations, the release rate modifier may include a hydrophilic agent. In some variations, the release rate modifier is a polyethylene glycol, e.g., a polyethylene glycol with a molecular weight of between about 3000 to about 13000, between about 3000 to about 11000, between about 3000 to about 9000, between about 3000 to about 7000, between about 3000 to about 5000, between about 5000 to about 13000, between about 5000 to about 11000, between about 5000 to about 9000, between about 5000 to about 7000, between about 7000 to about 13000, between about 7000 to about 11000, between about 7000 to about 9000, between about 9000 to about 13000, between about 9000 to about 11000, between about 11000 to about 13000, and the like. In some variations, the release rate modifier is a polyethylene glycol with a molecular weight of about 6000.

As mentioned herein throughout, the device may be configured to deliver multiple drugs. In some variations, multiple types of drug particles are contained within a single drug eluting layer or within the device body. In other variations, a device comprises a drug eluting layer that is discontinuous, having different sections containing different drugs. In these variations, the different sections may have different compositions, and thus may also provide differing release rates. In still other variations, multiple drug eluting layers may be used, where each layer contains a different drug or combination of drugs. Drug-releasing boluses, as described above, may also hold different drugs therein or may collectively release different drugs than those released by the drug eluting layer. In still other variations, the device itself may release a different drug or combination of drugs than those drugs released by a drug eluting layer or layers. Any combination of these variations may also be used to achieve the desired drug delivery profiles.

Illustrative Agents

The device may comprise any suitable drug or agent, or combination of drugs or agents, and the agent selected will largely be determined by the desired use of the device. The device may comprise one or more diagnostic agents, and may also comprise one or more therapeutic agents. Diagnostic agents may be used, for example, in diagnosing the presence, nature, and/or extent of a disease or medical condition in a subject. Conversely, a therapeutic agent may be used to treat or affect one or more diseases, conditions, sensations, or symptoms.

Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, fluorescence imaging, positron emission tomography (PET), radiofrequency (RF) and microwave laser. Diagnostic agents may also include any other agent useful in facilitating diagnosis of a disease or other condition in a patient, whether or not imaging methodology is employed.

Examples of specific diagnostic agents include radio-opaque materials such as iodine or iodine-derivatives, for example, iohexyl and iopamidol. Other diagnostic agents such as, for example, radioisotopes, are detectable by tracing radioactive emissions. Examples of agents detectable by MRI are generally paramagnetic agents including, but not limited to, gadolinium chelated compounds. An example of an agent detectable by ultrasound includes, but is not limited to, perflexane. An example of a fluorescence agent includes, but is not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

The device may also comprise any suitable therapeutic agent. Suitable classes of therapeutic agents include, for example, local anesthetics, painkillers/analgesics (e.g., anti-inflammatory agents, opiates, etc.), vasoconstrictors, anti-allergens, anti-cholinergic agents, antihistamines, anti-infectives, anti-platelet agents, anti-coagulants, anti-thrombic agents, anti-scarring agents, anti-proliferative agents, chemotherapeutic agents, anti-neoplastic agents, decongestants, hemostatic agents, healing promoting agents and vitamins (for example, retinoic acid, vitamin A, depaxapanthenol, vitamin B and their derivatives), hypersomolar agents, immunomodulators, immunosuppressive agents, and combinations and mixtures thereof. It should be appreciated that the devices described here may comprise any combinations of drugs or agents (e.g., a combination of two, three, or four or more drugs or agents). For example, the devices may comprise combinations of local anesthetics and analgesics, combinations of local anesthetics and antibiotics, combinations of local anesthetics and vasoconstrictors, combinations of analgesics and antibiotics, combinations of analgesics and vasoconstrictors, combinations of analgesics and antibiotics, combinations local anesthetics, antibiotics and vasoconstrictors, and the like.

Examples of local anesthetics suitable for use with the described methods and devices include, but are not limited to, ropivicaine, mepivicaine, bupivicaine, cocaine, procaine, etidocaine, lidocaine, prilocaine, articaine, amylocaine, benzocaine, butacaine, chloroprocaine, dimethocaine, meprylcaine, metabutoxycaine, orthocaine, propoxycaine, procaine, proxymetacaine, risocaine, tetracaine, tropane, cyclomethycaine, hexylcaine, piperocaine, articaine, carticaine, cinchocaine, etidocaine, trimecaine, iontocaine, combinations thereof and the like. Examples of suitable vasoconstrictors include, but are not limited to, epinephrine, levonordefrin, adrenaline derivatives thereof, combinations thereof, and the like.

Anti-infective agents generally include antibacterial agents, antifungal agents, antiparasitic agents, antiviral agents, and antiseptics. Anti-inflammatory agents generally include steroidal and nonsteroidal anti-inflammatory agents.

Examples of antiallergic agents that may be suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, actinomycin D, actinomycin IV, actinomycin $I_1$, actinomycin $X_1$, actinomycin $C_1$, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of prohealing agents include, but are not limited to, sirolimus, everolimus, temsiolimus, and vitamin A.

Examples of cytostatic or antiproliferative agents that may be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that may be suitable for use with the described methods and devices include, but are not limited to, aminoglycosides, amphenicols, ansamycins, β-lactams such as penicillins, lincosamides, macrolides, nitrofurans, quinolones, sulfonamides, sulfones, tetracyclines, vancomycin, and any of their derivatives, or combinations thereof. Examples of penicillins that may be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin.

Examples of antifungal agents suitable for use with the described methods and devices include, but are not limited to, allylamines, imidazoles, polyenes, thiocarbamates, triazoles, and any of their derivatives. Antiparasitic agents that may be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscarnet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazoly-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Analgesics may include opiates, anti-inflammatory agents, and other painkillers. Examples of suitable opiates, include, but are not limited to codeine, hydrocodone, dihydrocodeine, oxycodone, fentanyl, propoxyphene, meperedine, hydromorphone, thebaine, papaverine, morphine, acetyldihydrocodeine, buprenorphine, oxymorphone, nalbuphine, buprenorphine, dihydroetorphine, tramadol, derivates thereof, combinations thereof, and the like. Anti-inflammatory agents may include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Examples of suitable nonsteroidal anti-inflammatory agents include, but are not limited to, COX inhibitors. These COX inhibitors may include COX-1 or COX nonspecific inhibitors such as, for example, salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors may also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that may be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275295, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/congeners, derivatives of such compounds, and combinations thereof.

Examples of decongestants that may be used in the devices and methods described here include, but are not limited to, epinephrine, pseudoephedrine, oxymetazoline, phenylephrine, tetrahydrozolidine, and xylometazoline. Examples of mucolytics that may be used in the devices and methods described here include, but are not limited to, acetylcysteine, dornase alpha, and guaifenesin. Anti-histamines such as azelastine, diphenhydramine, and loratidine may also be used in the methods and devices described here.

Suitable hyperosmolar agents that may be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5, 5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

Materials

The devices described here may be made of any suitable material or combinations of material. In some variations, one or more of the materials may biodegradable, bioerodable, or otherwise erodable. In these variations, the rate of biodegradation of the degradable portions of the device may be affected by a number of factors including, but not limited to, the type of material from which the portion is formed, the size and shape of the device, and the deployment conditions. The devices described here may be made from a single material, or may be made from a combination of materials.

One or more portions of the device may comprise one or more polymers. A polymer may be biodegradable, but need not be. Examples of biodegradable polymers that may be suitable for use with the methods and devices describe here include, but are not limited to, aliginate, cellulose and ester, dextran, elastin, fibrin, hyaluronic acid, polyacetals, polyarylates (L-tyrosine-derived or free acid), poly($\alpha$-hydroxy-esters), poly($\beta$-hydroxy-esters), polyamides, poly(amino acid), polyalkanotes, polyalkylene alkylates, polyalkylene oxylates, polyalkylene succinates, polyanhydrides, polyanhydride esters, polyaspartimic acid, polybutylene diglycolate, poly(caprolactone), poly(caprolactone)/poly(ethylene glycol) copolymers, poly(carbonate), L-tyrosine-derived polycarbonates, polycyanoacrylates, polydihidropyrans, poly(dioxanone), poly-p-dioxanone, poly(epsilon-caprolactone), poly(epsilon-caprolactone-dimethyltrimethylene carbonate), poly(esteramide), poly(esters), aliphatic polyesters, poly(etherester), poly(ethylene glycol)/poly(orthoester) copolymers, poly(glutarunic acid), poly(glycolic acid), poly(glycolide), poly(glycolide)/poly(ethylene glycol) copolymers, poly(glycolide-trimethylene carbonate), poly(hydroxyalkanoates), poly(hydroxybutyrate), poly(hydroxybutyrate-co-valerate), poly(imino carbonates), polyketals, poly(lactic acid), poly(lactic acid-co-glycolic acid), poly(lactic acid-co-glycolic acid)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)/poly(ethylene glycol) copolymers, poly(lactide)/poly(glycolide) copolymers, polyorthoesters, poly(oxyethylene)/poly(oxypropylene) copolymers, polypeptides, polyphosphazenes, polyphosphoesters, polyphosphoester urethanes, poly(propylene fumarate-co-ethylene glycol), poly(trimethylene carbonate), polytyrosine carbonate, polyurethane, PorLastin or silk-ealastin polymers, spider silk, tephaflex, terpolymer (copolymers of glycolide, lactide or dimethyltrimethylene carbonate), and combinations, mixtures or copolymers thereof. Examples of nonbiodegradable polymers suitable for use with the methods and devices described herein include, but are not limited to poly(ethylene vinyl acetate), poly(vinyl acetate), silicone polymers, polyurethanes, polysaccharides such as a cellulosic polymers and cellulose derivatives, acyl substituted cellulose acetates and derivatives thereof, copolymers of poly(ethylene glycol) and poly(butylene terephthalate), polystyrenes, polyvinyl chloride, polyvinyl fluoride, poly(vinyl imidazole), chorosulphonated polyolefins, polyethylene oxide, and copolymers and blends thereof.

In other variations, one or more portions of the device comprise one or more metals, metallic materials, or metal alloys. Examples of suitable metals include, but are not limited to zinc, magnesium, cobalt, chromium, nickel, platinum, stainless steel, titanium, tantalum, and iron, combinations thereof and the like. Examples of suitable metal alloys include, but are not limited to, magnesium, nickel-cobalt alloys, nickel-titanium alloys, copper-aluminum-nickel alloys, copper-zinc-aluminum-nickel alloys, combinations thereof and the like. In still other variations, one or more portions of the device may comprise an elastomeric material.

In some variations, one or more portions of the device may comprise one or more hemostatic agents, which may help to stop or prevent bleeding. For example, the devices described here may comprise oxidated cellulose (e.g., OXYCEL®, SURGICEL NU-KNIT®), gelatin foams (e.g., GELFOAM®, SURGIFLO®, SURGIFOAM®, THROMBI-GEL®, THROMBINAR®), microfibrillar collagen (e.g., ACTIFOAM®, AVITENE®, COSTASIS®, HELISTAT®, INSTAT®), one or more sealants or adhesives (as described in more detail below), combinations thereof, and the like.

In some variations, one or more portions of the device comprise a mucoadhesive material or other adhesive material. For example, some devices comprise one or more mucoadhesive hydrogels, e.g., PLG polymers, polyacrylic acids, carageenan, alginate, xantham gum, carboxymethylcellulose, hydroxypropyl cellulose, chitins, chitosan, hyaluronic acids, lectins, their derivatives, combinations thereof, and the like. In other variations, the devices may comprise a fibrin glue, a cyanoacrylate glue, combinations thereof or the like. When the devices comprise a fibrin glue, the glue may be formed by mixing fibrinogen and thrombin. Fibrin glues may further comprise one or more clotting factors or other components of the clotting cascade (e.g., vitamin K, calcium, phospholipids, and the like), which may affect the strength or durability of the resulting polymerized fibrin. The fibrin glue may further comprise one or more anti-fibrinolytic agents (e.g., apoprotein), that may affect the rate of degradation/fibrolysis of the clot These adhesive materials may additionally be configured to release one or more drugs therefrom.

Methods

Also described here are methods for treating tonsillar tissue. Generally, the methods described here comprise implanting or delivering one or more of the devices described above to one or more areas of tonsillar tissue. For example, in some methods one or more tissue-piercing devices may be at least partially implanted into tonsillar tissue. In other methods, one or more clips or tissue-immobilizing devices may be anchored or otherwise connected to tissue. In still other methods, a plurality of space filling implants may be delivered in or around tonsillar tissue. In yet other methods, one or more gels, foams, patches, meshes, films, or sheets are implanted in, attached to, or otherwise delivered to tonsillar tissue. In still other variations, a combination of the aforementioned devices may be delivered to tonsillar tissue. Any of these devices may be administered to or implanted in any suitable area of tonsillar tissues. In some methods, one or more devices are applied to the tonsils, adenoids, lingual tonsils, or tubal tonsils. In other methods, one or more devices are applied to one or more portions of the tonsillar fossa, such as the palatopharyngeal arch, palatoglossal arch, and superior constrictor muscle, or other connective or surrounding tissue.

When one or more of the devices applied here are delivered to tonsillar tissues, these devices may be delivered to any suitable tissue at any suitable time. In some methods, one or more devices are delivered to one or more swollen or infected areas of tonsillar tissue. In some of these methods, the devices may provide one or more useful functions (e.g., reduce swelling) in anticipation of a tonsillar procedure such as a tonsillectomy. Indeed, in some variations the devices described here may be used to treat one or more conditions or symptoms associated therewith, such as, for example tonsillitis, obstructive sleep apnea, or the like. In other methods, one or more devices are delivered to tonsillar tissue during a tonsil procedure. For example, after at least a portion of the palatine tonsils are removed during a tonsillectomy, one or more devices may be delivered to the exposed tonsillar bed. In some instances, one or more of the devices may act to cover or seal the exposed tonsillar bed from external forces or stimuli. In still other methods, one or more devices are delivered to tonsillar tissue following a tonsil procedure. This may provide utility in the continued treatment of post-operative discomfort following a tonsil procedure. For example, if a patient is still experiencing discomfort a week after a tonsil procedure, one or more devices may be delivered to the tonsillar tissue to provide one or more painkillers. It should be appreciated that the devices may be delivered to tonsillar tissue at any combination of the time points described above (e.g., one or more devices are delivered prior to a tonsil procedure while one or more devices are delivered during a tonsil procedure, one or more devices are delivered during a tonsil procedure while one or more devices are delivered following a tonsil procedure, etc.). It should also be appreciated that one or more adhesives (e.g., a fibrin glue) may be used to cover or coat a portion of one or more of the devices described here, or may be used to help secure one or more of the devices to tissue. These adhesives may be further configured to release one or more drugs.

Generally, the devices described above may be configured to release one or more drugs to tonsillar tissues. In some variations, one or more drugs may treat inflammation or swelling of one or more tonsillar tissues. In other variations, the one or more drugs may help to aid in post-operative recovery following a tonsil procedure. More specifically, these methods may comprise administering one or more antibiotics, painkillers, hemostatic agents, pro-healing drugs or a combination thereof. As noted above, the devices may be administered before, during, or after a tonsillectomy, adenoidectomy, lingual tonsillectomy or any other tonsil procedure.

As mentioned above, some methods comprise at least partially implanting one or more tissue-piercing devices into tonsillar tissue. Any number of the tissue-piercing devices may be implanted into tissue, and each tissue-piercing device may have any suitable configuration of elements as described above. When multiple tissue-piercing devices are implanted into tonsillar tissue, the tissue-piercing devices may have the same configuration, or may have different configurations. When the tissue-piercing devices are configured to release one or more drugs over a period or periods of time, the tissue-piercing devices may release the same drugs over the same periods of time, or may deliver different drugs over different periods of time. For example, some tissue-piercing device may be configured to deliver an antibiotic over one period of time (e.g., 3 days), while others may be configured to deliver one or more painkillers or local anesthetics over a second period of time (e.g., 10 days). This potential variability in configurations between different tissue-piercing devices, as well as variability in drug-delivery from other devices described here, may grant a physician considerable leeway in tailoring a treatment regiment for an individual patient.

Figure 21A:
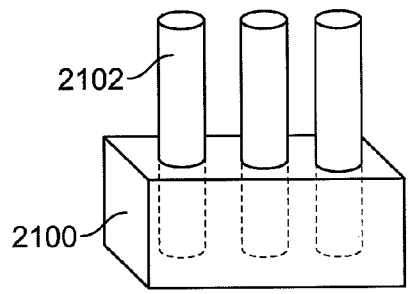
FIGS. 21A and 21B are illustrative depictions of suitable holders for use with the devices described here.
Figure 21B:
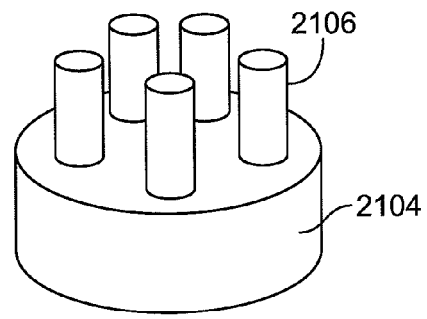

The tissue-piercing devices may be implanted into tissue in any suitable manner. The tissue-piercing devices may implanted simultaneously, or sequentially. In some variations, a batch of tissue-piercing devices are implanted simultaneously, but different batches are implanted sequentially. In some methods, one or more tissue-piercing devices may be introduced through a catheter via a pusher. In other methods, tissue-piercing devices are released from one or more guns or injector devices. In still other methods, a plurality of tissue-piercing devices may be released from a holder. The holder may be any suitable structure that is capable of releasably housing one or more tissue-piercing devices. A holder may have any suitable size or shape, and may be able to house any number of tissue-piercing devices. For example, FIG. 21A shows a block-shaped holder (2100) that is configured to hold three filaments (2102), while FIG. 21B shows a cylindrical holder (2104) configured to hold five filaments (2106).

Figure 22A:
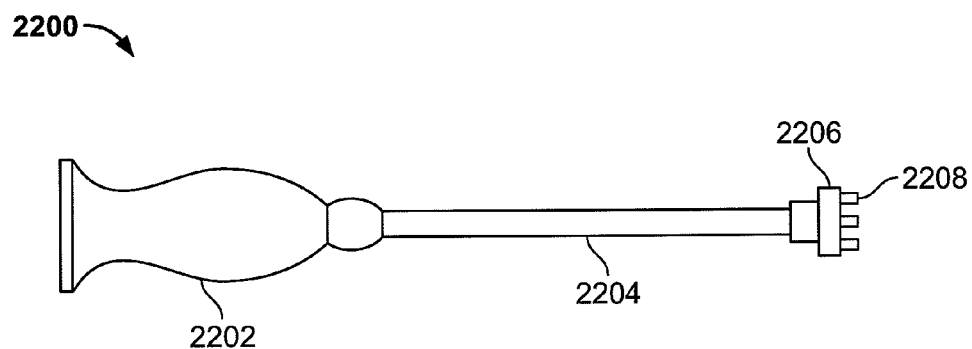
FIGS. 22A and 22B are illustrative depictions of suitable variations of delivery devices for use with the devices described here.
Figure 22B:
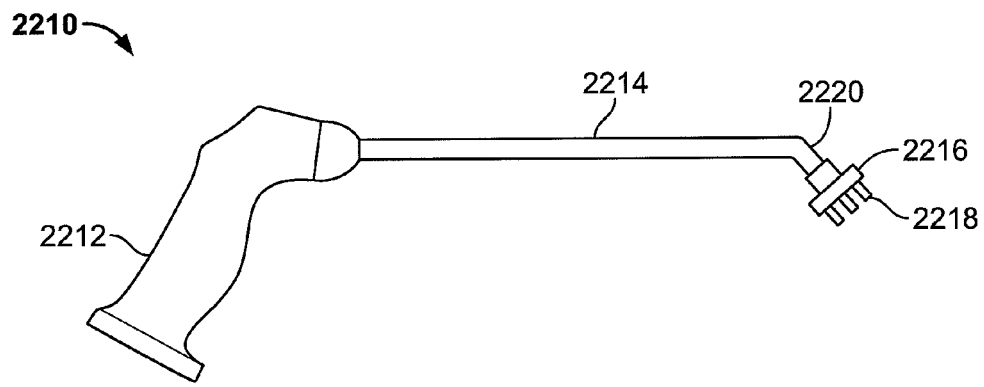

A holder may be releasably house at least a portion of one or more delivery devices. FIG. 22A illustrates a suitable variation of delivery device (2200). Shown there is handle (2202) and rod (2204), which is attached a holder (2206) housing a plurality of tissue-piercing devices (2208). While shown as being straight, rod (2204) may have one or more curves or angled portion. FIG. 22B shows one such variation of delivery device (2210) comprising handle (2212) and rod (2214). Also shown there is holder (2216) and tissue-piercing devices (2218). While shown in FIG. 22B as having one angled section (2220), rod (2214) may have any suitable number of angled or curved sections.

Figure 23A:
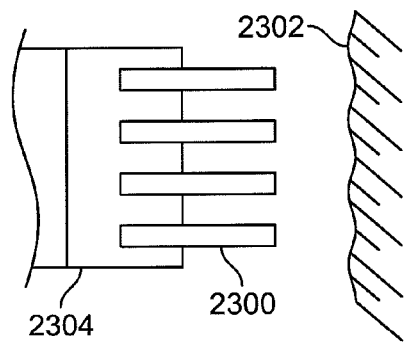
FIGS. 23A-23C and 24A-24C depict illustrative methods of delivering tissue-piercing devices to tissue.
Figure 23B:
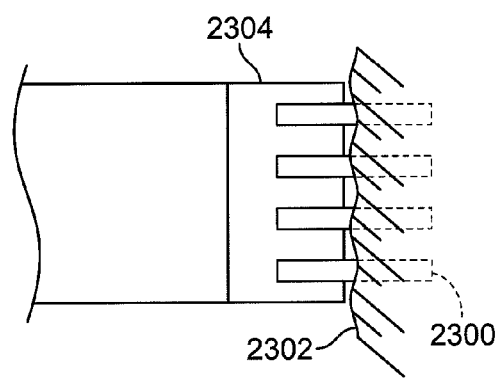
Figure 23C:
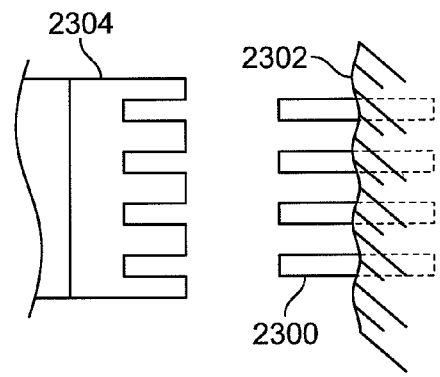

FIGS. 23A-23C illustrate one method of applying a plurality of tissue-piercing devices (2300) to tonsillar tissue (2302) from a holder (2304). Holder (2304) may be attached to any suitable delivery device, such as those described immediately above. First, holder (2304) and tissue-piercing devices (2300) are advanced to tonsillar tissue, as shown in FIG. 23A. The holder (2304) may then be further advanced, such that one or more of the tissue-piercing devices (2300) are pushed into the tonsillar tissue (2302), as shown in FIG. 23B. The tissue-piercing devices (2300) may then be disengaged from the holder (2304), such that the tissue-piercing devices are left at least partially implanted in tonsillar tissue (2302), as shown in FIG. 23C. The tissue-piercing devices (2300) may be disengaged from holder (2304) in any suitable manner. In some variations, the delivery device (not shown) may comprise one or more pushers (not shown) that force the tissue-piercing devices (2300) from holder (2304). In other variations, the tissue-piercing devices may be configured to be held inside tissue, as described in more detail above. Once the tissue-piercing devices (2300) are inserted into the tonsillar tissue (2302), the tissue-piercing devices (2300) may resist being pulled out of the tonsillar tissue (2302). Thus, when holder (2304) is pulled away from tonsillar tissue (2302), the tissue-piercing devices (2300) may be held in place such that they disengage from holder (2304).

Figure 24A:
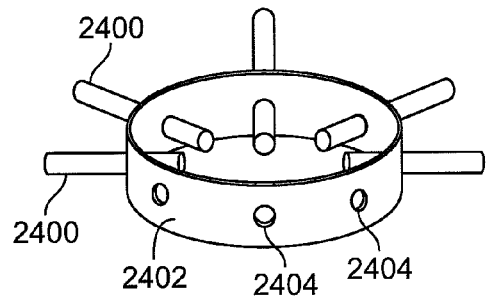
Figure 24B:
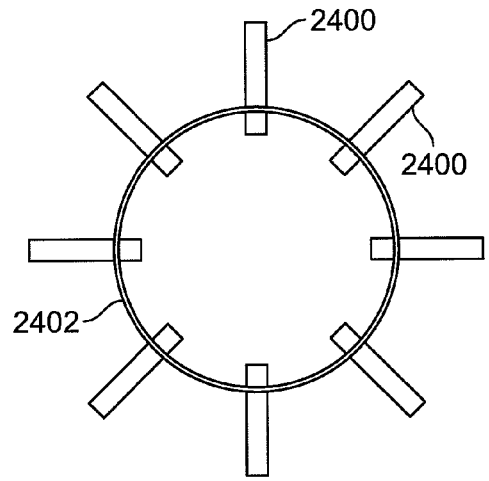
Figure 24C:
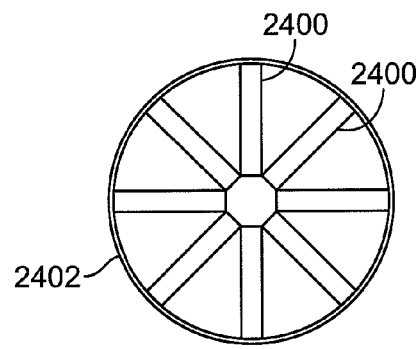

FIGS. 24A-24C illustrate another method by which a plurality of tissue-piercing devices (2400) may be implanted into tonsillar tissue (not shown). FIG. 24A shows a perspective view of hoop (2402) comprising apertures (2404). Also shown there are tissue-piercing devices (2400) at least partially disposed in apertures (2404). Generally each tissue-piercing device (2400) may be configured to slide or otherwise move through an aperture (2404) of hoop (2402). To implant tissue-piercing devices (2400) into tonsillar tissue, the tissue-piercing devices (2400) and hoop (2402) may first be placed in an "open" configuration where the majority of each tissue-piercing implant (2400) resides outside of the hoop (2402), as shown in a top view in FIG. 24B. The hoop (2402) may then be placed around a portion of tonsillar tissue, and the tissue-piercing implants (2400) may be moved to a "closed" configuration, in which a majority of each tissue-piercing device (2400) has been advanced into the hoop (2402) via apertures (2404), as shown in FIG. 24C. Moving tissue-piercing devices (2400) through apertures (2404) may cause the tissue-piercing devices to penetrate tonsillar tissue that is positioned inside of hoop (2402). In some variations, the tissue-piercing devices (2400) may pass entirely through apertures (2404) such that the hoop (2402) may be removed while leaving the tissue-piercing devices (2400) implanted in tissue. In other variations, one or more tissue-piercing devices (2400) remain connected to hoop (2402) such that hoop (2402) is held in place against tissue.

Although the foregoing invention has, for the purposes of clarity and understanding been described in some detail by way of illustration and example, it will be apparent that certain changes and modifications may be practiced, and are intended to fall within the scope of the appended claims.

We claim:

1. A method for treating a patient comprising:
    performing a tonsil procedure;
    at least partially delivering at least one drug-releasing implant to tonsillar tissue of the patient; and
    suturing one or more portions of a mucosal flap with one or more drug-releasing sutures to cover at least a portion of the at least one drug-releasing implant.

2. The method of claim 1 wherein the at least one drug-releasing implant comprises at least one polymer filament.

3. The method of claim 2 wherein the at least one polymer filament comprises one or more anchoring features that impair removal of the at least one polymer filament from the tonsillar tissue.

4. The method of claim 3 wherein the anchoring features comprises one or more notches in a surface of the at least one polymer filament.

5. The method of claim 3 wherein the anchoring feature comprises one or more barbs or prongs.

6. The method of claim 1 wherein the at least one drug-releasing implant comprises a suture.

7. The method of claim 1 wherein the at least one drug-releasing implant comprises a plurality of space-filling implants.

8. The method of claim 7 wherein the plurality of space-filling implants comprise one or more fibrin glue components.

9. The method of claim 1 further comprising covering at least a portion of the tonsillar tissue with one or more films, sheets, meshes, or patches.

10. The method claim 1 wherein the one or more drug-releasing implant comprises a clip, and wherein the clip comprises a surface member and at least one anchoring member.

11. The method of claim 1 further comprising affixing a tissue-restraining device to the tonsillar tissue.

12. The method of claim 1 wherein the at least one drug-releasing implant is configured to release an anti-inflammatory.

13. The method of claim 1 wherein the at least one drug-releasing implant is configured to release an antibiotic.

14. The method of claim 1 wherein the at least one drug-releasing implant is configured to release a painkiller or local anesthetic.

15. The method of claim 1 wherein the at least one drug-releasing implant is biodegradable.

16. The method of claim 1 wherein the at least one drug-releasing implant comprises a polymer.

17. The method of claim 1 wherein the tonsil procedure is a tonsillectomy or an adenoidectomy.

18. The method of claim 17 wherein the tonsillar tissue comprises a tonsillar bed.

19. The method of claim 17 wherein the tonsillar tissue comprises at least one of the palatoglossal arch and the palatopharyngeal arch.

20. The method of claim 1 wherein the tonsillar tissue comprises one or more tonsils or adenoids.

21. The method of claim 1 wherein the tonsillar tissue comprises the tonsillar fossa.

22. The method of claim 1 wherein at least partially delivering the at least one drug-releasing implant comprises implanting at least a portion of the at least one drug-releasing implant in tonsillar tissue.

23. The method of claim 1 wherein at least partially delivering the at least one drug-releasing implant comprises placing at least a portion of the at least one drug-releasing implant against a tonsillar tissue surface.

24. The method of claim 1 wherein the at least one drug-releasing implant comprises an adhesive.

25. The method of claim 24 wherein the adhesive is a fibrin glue.

26. The method of claim 1 wherein the at least one drug-releasing implant is configured to release a vasoconstrictor.

27. The method of claim 1 wherein the at least one drug-releasing implant comprises a hemostatic material.

28. The method of claim 1 wherein the at least one drug-releasing implant is configured to reduce the size of clots formed on or in the tonsillar tissue.

29. The method of claim 1 wherein the at least one drug-releasing implant is configured to prevent or reduce bleeding.

* * * * *